(12) United States Patent
Gerardo et al.

(10) Patent No.: US 10,598,632 B1
(45) Date of Patent: Mar. 24, 2020

(54) LAYERED STRUCTURE AND METHOD FOR FABRICATING SAME

(71) Applicant: The University of British Columbia, Vancouver (CA)

(72) Inventors: Carlos D. Gerardo, Vancouver (CA); Robert Rohling, Vancouver (CA); Edmond Cretu, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 16/684,543

(22) Filed: Nov. 14, 2019

Related U.S. Application Data

(60) Division of application No. 16/276,548, filed on Feb. 14, 2019, now Pat. No. 10,509,013, which is a
(Continued)

(51) Int. Cl.
*G01N 29/24* (2006.01)
*G01N 29/06* (2006.01)
(Continued)

(52) U.S. Cl.
CPC ....... *G01N 29/2406* (2013.01); *B06B 1/0292* (2013.01); *B81B 3/0021* (2013.01); *B81C 1/00166* (2013.01); *G01N 29/0654* (2013.01); *H01L 41/0973* (2013.01); *H01L 41/27* (2013.01)

(58) Field of Classification Search
CPC ............ G01N 29/2406; G01N 29/0654; H01L 41/27; H01L 41/0973; B81B 3/0021; B81C 1/00166; B06B 1/0292
See application file for complete search history.

(56) References Cited

U.S. PATENT DOCUMENTS 5,281,635 A   1/1994   Bishop
6,328,696 B1  12/2001  Fraser
(Continued)

FOREIGN PATENT DOCUMENTS

CN   105413997         3/2016
WO   WO-2019119127 A1 * 6/2019  ............. B32B 27/00

OTHER PUBLICATIONS

Asaoka, et al., "Cavity Shape Control of the Roll-to-Roll Fabricated Novel Microstructure Film for Improving the Viewing-Angle Characteristics of LCDs," SID Symposium Digest of Technical Papers, vol. 45, No. 1, Jun. 2014, pp. 17-20.
(Continued)

*Primary Examiner* — Daniel Pihulic
(74) *Attorney, Agent, or Firm* — Benedict R. Dugan; Lowe Graham Jones PLLC

(57) ABSTRACT

Methods and techniques for fabricating layered structures, such as capacitive micromachined ultrasound transducers, as well as the structures themselves. The layered structure has a membrane that includes a polymer-based layer and a top electrode on the polymer-based layer. The membrane is suspended over a closed cavity and may be actuated by applying a voltage between the top electrode and a bottom electrode that may be positioned along or be a bottom of the closed cavity. The layered structure may be fabricated using a wafer bonding process.

16 Claims, 16 Drawing Sheets

Related U.S. Application Data continuation of application No. PCT/CA2018/051618, filed on Dec. 18, 2018.

(60) Provisional application No. 62/607,641, filed on Dec. 19, 2017.

(51) Int. Cl.

| | |
|---|---|
| H01L 41/27 | (2013.01) |
| H01L 41/09 | (2006.01) |
| B81C 1/00 | (2006.01) |
| B81B 3/00 | (2006.01) |
| B06B 1/02 | (2006.01) |

(56) References Cited

U.S. PATENT DOCUMENTS

| | | | |
|---|---|---|---|
| 7,673,375 | B2 | 3/2010 | Chang et al. |
| 7,898,722 | B2 | 3/2011 | Miles |
| 8,783,113 | B2 | 7/2014 | Robert et al. |
| 8,857,041 | B2 | 10/2014 | Masaki et al. |
| 8,926,517 | B2 | 1/2015 | Huang |
| 8,939,029 | B2 | 1/2015 | Zhang et al. |
| 9,085,456 | B2 | 7/2015 | Tsai et al. |
| 9,925,561 | B2 | 3/2018 | Emadi et al. |
| 10,509,013 | B2* | 12/2019 | Gerardo ............. G01N 29/2406 |
| 2005/0177045 | A1 | 8/2005 | Degertekin et al. |
| 2007/0013266 | A1 | 1/2007 | Chang et al. |
| 2008/0194053 | A1 | 8/2008 | Huang |
| 2009/0324834 | A1 | 12/2009 | Hanson |
| 2010/0058865 | A1 | 3/2010 | Zhang et al. |
| 2015/0174573 | A1 | 6/2015 | Esch |
| 2017/0162439 | A1 | 6/2017 | Miki et al. |
| 2017/0232474 | A1 | 8/2017 | Oralkan et al. |
| 2019/0133553 | A1 | 5/2019 | Belt et al. |
| 2019/0187101 | A1* | 6/2019 | Gerardo ................ G01H 11/06 |
| 2019/0187102 | A1* | 6/2019 | Gerardo ............. G01N 29/2406 |

OTHER PUBLICATIONS

Bozkurt, et al., "Theory and Analysis of Electrode Size Optimization for Capacitive Microfabricated Ultrasonic Transducers," IEEE Transactions on Ultrasonics, Ferroelectrics, and Frequency Control, vol. 46, No. 6, Nov. 1999, pp. 1364-1374.
Chang, et al., "A Novel Method for Fabricating Sonic Paper," 2007 IEEE Ultrasonics Symposium Proceedings, 2007, pp. 527-530.
Chang, et al., "An adaptive sparse deconvolution method for distinguishing the overlapping echoes of ultrasonic guided waves for pipeline crack inspection," Meas. Sci. Technol., vol. 28, No. 3, 2017, 035002, 14 pages.
Chang, et al., "Polymer-based Capacitive Micromachined Ultrasonic Transducers (CMUT) for Micro Surgical Imaging Applications," Proceedings of the 1st IEEE International Conference on Nano/Micro Engineered and Molecular Systems, Jan. 18-21, 2006, China, pp. 61-65.
Chen, et al., "Fabrication of a Curved Row-Column Addressed Capacitive Micromachined Ultrasonic Transducer Array," J. of Microelectromechanical Systems, vol. 25, No. 4, Aug. 2016, pp. 675-682.
Chiamori, et al., "Suspension of nanoparticles in SU-8: Processing and characterization of nanocomposite polymers," Microelectronics Journal, vol. 39, No. 2, Feb. 2008, pp. 228-236.
Chiou, et al., "Characterization and Optimization Design of the Polymer-Based Capacitive Micro-Arrayed Ultrasonic Transducer," Japanese J. Appl. Phys., vol. 46, No. 11, 2007, pp. 7496-7503.
Chiou, et al., "Finite element modeling, characterization, and optimization design for the polymer-typed capacitive micro-arrayed ultrasonic transducer," Microsyst Technol, vol. 14, No. 6, Jun. 2008, pp. 787-797.
Chiriacò, et al., "Fabrication of interconnected multilevel channels in a monolithic SU-8 structure using a LOR sacrificial layer," Microelectronic Engineering, vol. 164, Oct. 2016, pp. 30-35.

Chiu, et al., "Implementation of ultrasonic touchless interactive panel using the polymer-based CMUT array," IEEE Sensors 2009 Conference, 2009, pp. 625-630.
Culjat, et al., "Polyimide-Based Conformal Ultrasound Transducer Array for Needle Guidance," IEEE Sensors Journal, vol. 9, No. 10, Oct. 2009, pp. 1244-1245.
Daft, et al. "Conformable transducers for large-volume, operator-independent imaging," 2010 IEEE International Ultrasonics Symposium Proceedings, 2010, pp. 798-808.
Dalziel, "Electric shock hazard," IEEE Spectrum, vol. 9, No. 2, Feb. 1972, pp. 41-50.
Ergun, et al., "Capacitive Micromachined Ultrasonic Transducers: Fabrication Technology," IEEE Transactions on Ultrasonics, Ferroelectrics, and Frequency Control, vol. 52, No. 12, Dec. 2005, pp. 2242-2258.
Foulds, et al., "Polydimethylglutarimide (PMGI) as a sacrificial material for SU-8 surface-micromachining," J. Micromech. Microeng., vol. 18, No. 7, 2008, 075011, 11 pages.
Galisultanov, et al., "Dynamic Characteristics of Circular CMUTs with Air-Filled Cavities," 2016 IEEE International Ultrasonics Symposium Proceedings, 2016, 4 pages.
Hatzakis, et al., "Single-Step Optical Lift-Off Process," IBM J. Res. Develop., vol. 24, No. 4, Jul. 1980, pp. 452-460.
Ho, et al., "Long-term measurement results of pre-charged CMUTs with zero external bias operation," Stanford University, California, USA; Brandenburg University of Technology, Cottbus, Germany, 2012, 4 pages.
Huang, et al., "A Solution to the Charging Problems in Capacitive Micromachined Ultrasonic Transducers," IEEE Transactions on Ultrasonics, Ferroelectrics, and Freqquency Control, vol. 52, No. 4, Apr. 2005, pp. 578-580.
Iniewski, "Medical imaging: principles, detectors, and electronics," 7.4.1 Acoustic Characteristics, John Wiley & Sons, 2009, p. 186.
Jeanne, et al., "Evaluation of Parylene as Protection Layer for Capacitive Micromachined Ultrasonic Transducers," ECS Transactions, vol. 11, No. 16, 2008, pp. 25-33.
Joseph, et al., "A Low Pull-in SU-8 based Capacitive Micromachined Ultrasonic Transducer for Medical Imaging Applications," 2014 36th Annual International Conference of the IEEE Engineering in Medicine and Biology Society (EMBC), 2014, pp. 1398-1401.
Joseph, et al., "Fabrication and characterization of SU-8-based capacitive micromachined ultrasonic transducer for airborne applications," J. Micro/Nanolith. MEMS MOEMS 17(1), Jan.-Mar. 2018, 015003, 10 pages.
Joseph, et al., "Fabrication of SU-8 Based Capacitive Micromachined Ultrasonic Transducer for Low Frequency Therapeutic Applications," 2015 37th Annual International Conference of the IEEE Engineering in Medicine and Biology Society (EMBC), 2015, pp. 1365-1368.
Joshi, et al., "Conformable Body Patches for Ultrasound Applications," 2015 IEEE 17th Electronics Packaging and Technology Conference (EPTC), 2015, pp. 1-4.
Kshirsagar, et al., "Pre-Charged CMUTs with Efficient Low-Bias Voltage Operation for Medical Applications," 2013 Joint UFFC, EFTF and PFM Symposium, IEEE, 2013, pp. 1728-1730.
Li, et al., "Design and Analysis of Capacitive Micromachined Ultrasonic Transducers Based on SU-8," Key Engineering Materials, vols. 645-646, May 2015, pp. 577-582.
Liu, "Recent Developments in Polymer MEMS," Adv. Mater., vol. 19, No. 22, Nov. 2007, pp. 3783-3790.
Lorenz, et al., "SU-8: a low-cost negative resist for MEMS," J. Micromech. Microeng., vol. 7, No. 3, 1997, pp. 121-124.
MicroChem: Innovative Chemical Solutions for MEMS and Microelectronics, Newton, Massachusetts, available at http://www.microchem.com/, accessed on Sep. 4, 2017, 7 pages.
Moser, et al., "Suspended SU-8 structures for monolithic microfluidic channels," Microfluidics and Nanofluidics, vol. 10, No. 1, 2011, pp. 219-224.
Oralkan, et al. "Capacitive Micromachined Ultrasonic Transducers: Next-Generation Arrays for Acoustic Imaging?," IEEE Transactions on Ultrasonics, Ferroelectrics and Frequency Control, vol. 49, No. 11, Nov. 2002, pp. 1596-1610.

(56) References Cited

OTHER PUBLICATIONS

Oralkan, et al., "High-Frequency CMUT Arrays for High-Resolution Medical Imaging," 2004 IEEE Ultrasonics Symposium, 2004, pp. 399-402.
"Overview of Ultrasound Imaging Systems and the Electrical Components Required for Main Subfunctions," Tutorial, Maxim, available at https://www.maximintegrated.com/en/app-notes/index.mvp/id/4696, accessed on Nov. 3, 2017, 8 pages.
Pang, et al., "Development of a Novel Transparent Flexible Capacitive Micromachined Ultrasonic Transducer," Sensors (Basel), Jun. 2017, 17(6), 1443, 17 pages.
Park, et al., "Zero-Bias Resonant Sensor with an Oxide-Nitride Layer as Charge Trap," IEEE Sensors 2010 Conference, 2010, pp. 1024-1028.
Rouyer, et al., "Conformal Ultrasound Imaging System for Anatomical Breast Inspection," IEEE Transactions on Ultrasonics, Ferroelectrics, and Frequency Control, vol. 59, No. 7, Jul. 2012, pp. 1457-1469.
Salvo, et al., "Adhesive bonding by SU-8 transfer for assembling microfluidic devices," Microfluid Nanofluid, vol. 13, No. 6, Dec. 2012, pp. 987-991.
Seidemann, et al., "SU8-micromechanical structures with in situ fabricated movable parts," Microsystem Technologies, vol. 8, No. 4-5, Aug. 2002, pp. 348-350.
Singh, et al., "Conformal Ultrasound Imaging System," Acoustical Imaging, M. P. André, J. P. Jones, and H. Lee, Eds. Springer Netherlands, 2011, pp. 211-222.
Song, et al., "Use of a photoresist sacrificial layer with SU-8 electroplating mould in MEMS fabrication," J. Micromech. Microeng., vol. 13, No. 6, 2003, pp. 816-821.
Spratley, et al., "Highly Flexible SU-8 Microstructures," Transducers 2007, 2007 International Solid-State Sensors, Actuators and Microsystems Conference, IEEE, 2007, pp. 587-590.
Wang, et al., "SU-8-Based Nanocomposites for Acoustical Matching Layer," IEEE Transactions on Ultrasonics, Ferroelectrics, and Frequency Control, vol. 56, No. 7, Jul. 2009, pp. 1483-1489.
Wong, et al., "Evaluation of Wafer Bonded CMUTs with Rectangular Membranes Featuring High Fill Factor," IEEE Transactions on Ultrasonics, Ferroelectrics, and Frequency Control, vol. 55, No. 9, Sep. 2008, pp. 2053-2065.
Yeh, et al., "High-frequency CMUT arrays for high-resolution medical imaging," Medical Imaging 2005: Ultrasonic Imaging and Signal Processing, edited by William F. Walker, Stanislav Y. Emelianov, Proc. of SPIE vol. 5750, Bellingham, WA, 2005, pp. 87-98.
Zhang, et al., "An Optically Transparent Capacitive Micromachined Ultrasonic Transducer (CMUT) Fabricated Using SU-8 or BCB Adhesive Wafer Bonding," in 2017 IEEE International Ultrasonics Symposium (IUS), 2017, 4 pages.
Zhuang, et al., "Flexible Transducer Arrays with Through-Wafer Electrical Interconnects Based on Trench Refilling with PDMS," 2007 IEEE 20th International Conference on Micro Electro Mechanical Systems (MEMS), Kobe, Japan, Jan. 2007, pp. 73-76.
Sadat, David, "Simulation of a Capacitive Micromachined Ultrasonic Transducer with a Parylene Membrane and Graphene Electrodes" (2012). Electronic Theses and Dissertations, 4824. http://stars.library.ucf.edu/etd/4824, 127 pages.
Salim, Muhammed Sabri et al., "Capacitive Micromachined Ultrasonic Transducers: Technology and Application," J. of Medical Ultrasound (2012) 20, pp. 8-31.
International Search Report and Written Opinion of the International Searching Authority dated Mar. 28, 2019, in International Patent Application No. PCT/CA2018/051618, 11 pages.

* cited by examiner

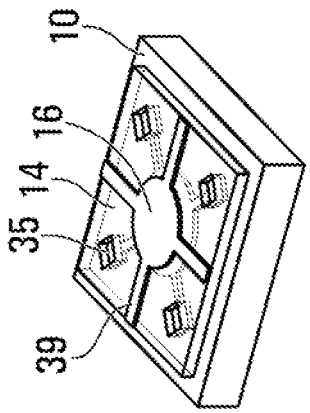
FIG. 32
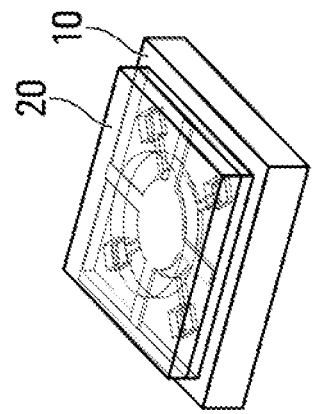
FIG. 33
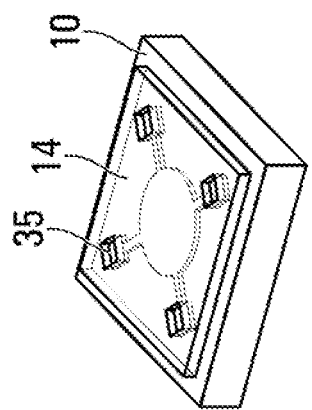
FIG. 34
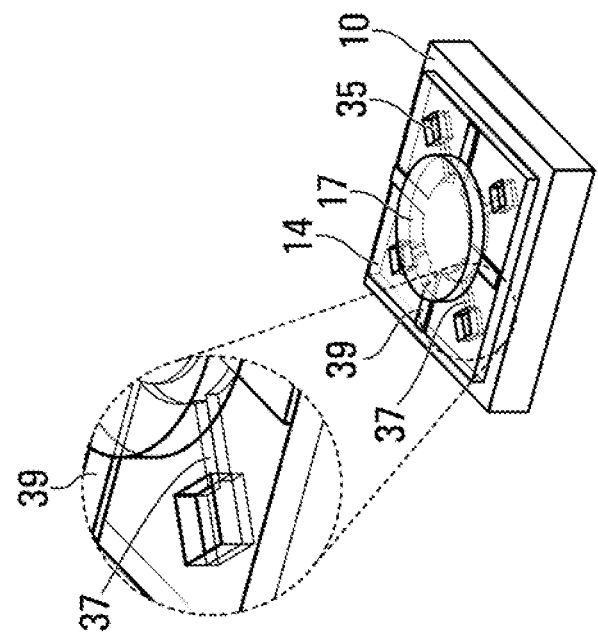
FIG. 35
FIG. 36
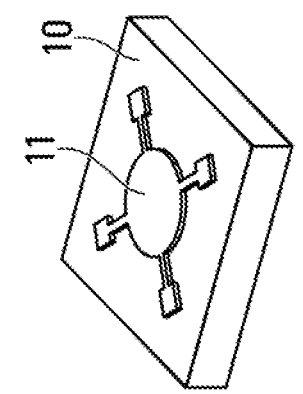
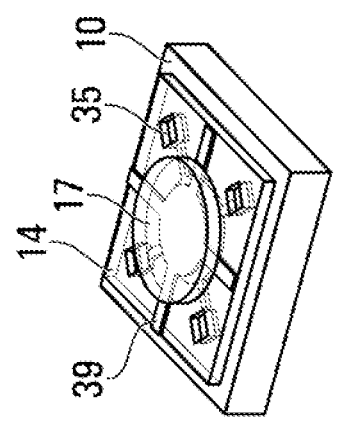
FIG. 37

LAYERED STRUCTURE AND METHOD FOR FABRICATING SAME

CROSS-REFERENCE TO RELATED APPLICATIONS

This application is a divisional of U.S. patent application Ser. No. 16/276,548, filed on Feb. 14, 2019, and entitled "Layered Structure and Method for Fabricating Same," which is a continuation of international application no. PCT/CA2018/051618, filed on Dec. 18, 2018, and entitled "Layered Structure and Method for Fabricating Same", which claims priority to U.S. provisional patent application No. 62/607,641, filed on Dec. 19, 2017, and entitled "Layered Structure and Method for Fabricating Same", the contents of which applications are incorporated herein by reference in their entireties.

TECHNICAL FIELD

The present disclosure is directed at methods, systems, and techniques for fabricating a layered structure, such as a capacitive micromachined ultrasound transducer, and the structure itself.

BACKGROUND

Ultrasound imaging is the most widely used medical imaging modality in the world in terms of images created annually. Ultrasound is useful for generating images of a variety of different targets within the human body. It is important that images are acquired with high quality and in an accessible, cost-effective manner since ultrasonic imaging has many medical uses. The ultrasound transducer is the key hardware involved sending and receiving ultrasonic waves to and from the body. Consequently, there exists a continued need to improve the capabilities of the transducer.

SUMMARY

According to a first aspect, there is provided a method for fabricating a capacitive micromachined ultrasound transducer, the method comprising: depositing a sacrificial layer on a substrate assembly that functions as a bottom electrode; patterning the sacrificial layer to be shaped as a cavity of the transducer; depositing a first polymer-based layer on the sacrificial layer; patterning a via hole through the first polymer-based layer to the sacrificial layer; patterning a top electrode on the first polymer-based layer above the sacrificial layer; depositing a second polymer-based layer on the top electrode such that the top electrode is between the first and second polymer-based layers; using the via hole, etching away the sacrificial layer to form the cavity of the transducer; and closing the cavity.

The top electrode may be embedded within the first and second polymer-based layers.

Patterning the sacrificial layer to be shaped as the cavity of the transducer, etching away the sacrificial layer to form the cavity of the transducer, and patterning the via hole, may be performed using organic and non-toxic solvents.

The first polymer-based layer may be photosensitive, and patterning the via hole may comprise: cross-linking a portion of the first polymer-based layer to remain following the patterning by exposing the portion to ultraviolet radiation; and applying a photoresist developer to etch away the first polymer-based layer that is blocking the via hole. The portion to remain may exclude the first polymer-based layer blocking the via hole.

The sacrificial layer may not be photosensitive and patterning the sacrificial layer to form the cavity may comprise: cross-linking a portion of the sacrificial layer shaped as the first shape; and applying a developer to etch away a portion of the sacrificial layer that is not cross-linked.

The sacrificial layer may not be photosensitive and patterning the sacrificial layer to be shaped as a cavity of the transducer may comprise: depositing a positive photoresist layer on the sacrificial layer; cross-linking a portion of the positive photoresist layer corresponding to a portion of the sacrificial layer that is shaped as the cavity; applying a photoresist developer to etch away the photoresist layer that is not cross-linked and the sacrificial layer that underlies the photoresist layer that is not cross-linked; and after the photoresist layer and the sacrificial layer have been etched away, removing the photoresist layer that is cross-linked.

The second polymer-based layer may be thicker than the first polymer-based layer.

The second polymer-based layer may be at least five times thicker than the first polymer-based layer.

The relative thickness of the second polymer-based layer to the first polymer-based layer may be selected such that the top electrode resonates at a frequency of at least 1 MHz.

The fabrication may be performed at a temperature of no more than 150° C.

The substrate assembly may be flexible.

The top electrode may comprise a conductive polymer.

The substrate assembly may comprise an optically-transparent material.

The substrate assembly may further comprise an optically-transparent conductive bottom electrode on the substrate.

Closing the cavity may comprise encapsulating the first and second polymer-based layers with a bio-compatible material.

The bio-compatible material may comprise a poly(p-xylylene) polymer.

Patterning the top electrode may comprise patterning metallic connections to the top electrode. The metallic connections may be uncovered by the second polymer-based layer after the cavity is closed, and closing the cavity may comprise depositing the bio-compatible material over the metallic connections.

Closing the cavity may be done in a polymer evaporator chamber at pressure of no more than 0.001 Torr.

After the sacrificial layer has been etched away, trapping charge in the first polymer-based layer may be done by: applying a voltage across the top electrode and the substrate assembly such that a portion of the first polymer-based layer contacting the top electrode may be pulled into contact with the substrate assembly; maintaining the portion of the first polymer-based layer contacting the top electrode and the substrate assembly in contact for a period of time; and then ceasing applying the voltage.

The sacrificial layer may comprise a polymer.

Depositing the sacrificial layer may comprise spray coating the polymer comprising the sacrificial layer on to the substrate assembly.

Depositing the first polymer-based layer on the sacrificial layer may comprise covering all surfaces of the sacrificial layer except a bottom surface contacting the substrate assembly with the first polymer-based layer.

The substrate assembly may comprise a conductive substrate.

The substrate assembly may comprise a non-conductive substrate and a conductive bottom electrode on the substrate.

Closing the cavity may comprise forming a watertight seal around the cavity.

The sacrificial layer may be non-reactive when exposed to the first and second polymer-based layers and to a photoresist developer used during the patterning of the first and second polymer-based layers, and the first and second polymer-based layers may be non-reactive when exposed to an etchant used to etch away the sacrificial layer.

The first and second polymer-based layers may comprise SU8 photoresist.

The sacrificial layer may comprise an OmniCoat™ composition.

The cavity may have a height selected such that an operating voltage of the transducer is no more than 50 Volts.

The cavity may have a height of no more than 0.3 µm.

Depositing the sacrificial layer may comprise evaporating a composition that comprises a solvent, and then depositing the composition as the sacrificial layer. At least 70% and no more than 90% of the solvent may be evaporated.

According to another aspect, there is provided a method for fabricating a capacitive micromachined ultrasound transducer, the method comprising: depositing a first polymer-based layer on a substrate assembly that functions as a bottom electrode; patterning the first polymer-based layer to be a cavity of the transducer; depositing a sacrificial layer on a separate substrate; depositing a second polymer-based layer over the sacrificial layer; depositing a top electrode on the second polymer-based layer; depositing a third polymer-based layer on the top electrode such that the top electrode is between the second and third polymer-based layers; adhering the first and third polymer-based layers together such that the cavity is closed; and etching away the sacrificial layer such that the second polymer-based layer is released from the separate substrate.

The top electrode may be embedded within the second and third polymer-based layers.

The method may further comprise cross-linking the first and third polymer-based layers prior to adhering the first and third polymer layers together.

Patterning the first polymer-based layer and etching away the sacrificial layer may be performed using organic and non-toxic solvents.

The first polymer-based layer may be photosensitive, and patterning the first polymer-based layer to be the cavity of the transducer may comprise: cross-linking a portion of the first polymer-based layer to remain following the etching by exposing the portion to ultraviolet radiation; and applying a photoresist developer to etch uncrossed-linked areas of the first polymer-based layer.

The second polymer-based layer may be thicker than the third polymer-based layer.

The second polymer-based layer may be at least five times thicker than the third polymer-based layer.

Relative thickness of the second polymer-based layer to the third polymer-based layer may be selected such that the top electrode resonates at a frequency of at least 1 MHz.

The fabrication may be performed at a temperature of no more than 150° C.

The substrate assembly may be flexible and bonded to a rigid carrier.

The top electrode may comprise a conductive polymer.

The substrate assembly may comprise an optically-transparent material.

The substrate assembly may further comprise an optically-transparent conductive bottom electrode on the substrate.

Adhering the first and third polymer layers together may comprise: treating surfaces of the first and third polymer layers to be adhered to each other with plasma; aligning the surfaces to each other; and pressing the surfaces together.

The adhering may be done in a bonding chamber at pressure of no more than 0.001 Torr.

The method may further comprise, after the adhering, trapping charge in the first polymer-based layer by: applying a voltage across the top electrode and the substrate assembly such that a portion of the first polymer-based layer contacting the top electrode is pulled into contact with the substrate assembly; maintaining the portion of the first polymer-based layer contacting the top electrode and the substrate assembly in contact for a period of time; and then ceasing applying the voltage.

The sacrificial layer may comprise a polymer.

Depositing the second polymer-based layer on the sacrificial layer may comprise completely covering the sacrificial layer with the second polymer-based layer.

The substrate assembly may comprise a conductive substrate.

The substrate assembly may comprise a non-conductive substrate and a conductive bottom electrode on the substrate.

Following the adhering a watertight seal may be around the cavity.

The sacrificial layer may be non-reactive when exposed to the second polymer-based layer and to a photoresist developer used during the patterning of the second polymer-based layer. The second polymer-based layer may be non-reactive when exposed to an etchant used to etch away the sacrificial layer.

The first, second, and third polymer-based layers may comprise SU8 photoresist.

The sacrificial layer may comprise an OmniCoat™ composition.

The cavity may have a height selected such that an operating voltage of the transducer is no more than 50 Volts.

The cavity may have a height of no more than 0.3 µm.

Depositing the sacrificial layer may comprise evaporating a composition that comprises a solvent, and then depositing the composition as the sacrificial layer. At least 70% and no more than 90% of the solvent may be evaporated.

According to another aspect, there is provided a method for fabricating a layered structure, the method comprising: depositing a sacrificial layer on a substrate assembly that functions as a bottom electrode; patterning the sacrificial layer into a first shape; depositing a first polymer-based layer on the sacrificial layer; patterning a top electrode on the first polymer-based layer above the sacrificial layer; depositing a second polymer-based layer on the top electrode such that the electrode is between the first and second polymer-based layers; and etching away the sacrificial layer to form a cavity under the electrode.

The electrode may be embedded within the first and second polymer-based layers.

The first shape may comprise a conduit extending through first polymer-based layer and permitting etchant to flow from a top of the first polymer-based layer to the sacrificial layer.

The second polymer-based layer may be deposited to block the conduit, and the method may further comprise etching away a portion of the second polymer-based layer that blocks the conduit. Etching away the sacrificial layer may comprise flowing the etchant through the conduit.

Patterning the sacrificial layer into the first shape and etching away the sacrificial layer to form the cavity may be performed using organic and non-toxic solvents.

The sacrificial layer may not be photosensitive and patterning the sacrificial layer to form the cavity may comprise: cross-linking a portion of the sacrificial layer shaped as the first shape; and applying a developer to etch away a portion of the sacrificial layer that is not cross-linked.

The sacrificial layer may not be photosensitive and patterning the sacrificial layer to form the cavity may comprise: depositing a positive photoresist layer on the sacrificial layer; cross-linking a portion of the positive photoresist layer corresponding to a portion of the sacrificial layer that is shaped as the cavity; applying a photoresist developer to etch away the photoresist layer that is not cross-linked and the sacrificial layer that underlies the photoresist layer that is not cross-linked; after the photoresist layer and the sacrificial layer have been etched away, removing the photoresist layer that is cross-linked.

The second polymer-based layer may be thicker than the first polymer-based layer.

The second polymer-based layer may be at least five times thicker than the first polymer-based layer.

Relative thickness of the second polymer-based layer to the first polymer-based layer may be selected such that the top electrode resonates at a frequency of at least 1 MHz.

The fabrication may be performed at a temperature of no more than 150° C.

The substrate assembly may be flexible.

The top electrode may comprise a conductive polymer.

The substrate assembly may comprise an optically-transparent material.

The substrate assembly may further comprise an optically-transparent conductive bottom electrode on the substrate.

The method may further comprise closing the cavity.

Closing the cavity may comprise encapsulating the first and second polymer-based layers with a bio-compatible material.

The bio-compatible material may comprise a poly(p-xylylene) polymer.

Patterning the top electrode may comprise patterning metallic connections to the top electrode. The metallic connections may be uncovered by the second polymer-based layer after the cavity is closed, and closing the cavity may comprise depositing the bio-compatible material over the metallic connections.

Closing the cavity may be done in a polymer evaporator chamber at a pressure of no more than 0.001 Torr.

Closing the cavity may comprise forming a watertight seal around the cavity.

The method may further comprise, after the sacrificial layer has been etched away, trapping charge in the first polymer-based layer may occur by: applying a voltage across the top electrode and the substrate assembly such that a portion of the first polymer-based layer contacting the top electrode is pulled into contact with the substrate assembly; maintaining the portion of the first polymer-based layer contacting the top electrode and the substrate assembly in contact for a period of time; and then ceasing applying the voltage.

The sacrificial layer may comprise a polymer.

Depositing the sacrificial layer may comprise spray coating the polymer comprising the sacrificial layer on to the substrate assembly.

Depositing the first polymer-based layer on the sacrificial layer may comprise covering all surfaces of the sacrificial layer except a bottom surface contacting the substrate assembly with the first polymer-based layer.

The substrate assembly may comprise a conductive substrate.

The substrate assembly may comprise a non-conductive substrate and a conductive bottom electrode on the substrate.

The sacrificial layer may be non-reactive when exposed to the first and second polymer-based layers and to a photoresist developer used during the patterning of the first and second polymer-based layers, and the first and second polymer-based layers may be non-reactive when exposed to an etchant used to etch away the sacrificial layer.

The first and second polymer-based layers may comprise SU8 photoresist.

The sacrificial layer may comprise an OmniCoat' composition.

The cavity may have a height selected such that an operating voltage of the structure is no more than 50 Volts.

The cavity may have a height of no more than 0.3 μm.

Depositing the sacrificial layer may comprise evaporating a composition that comprises a solvent, and then depositing the composition as the sacrificial layer. At least 70% and no more than 90% of the solvent may be evaporated.

According to another aspect, there is provided a method for fabricating a layered structure, the method comprising: depositing a first polymer-based layer on a substrate assembly that functions as a bottom electrode; patterning the first polymer-based layer to be a cavity; depositing a sacrificial layer on a separate substrate; depositing a second polymer-based layer over the sacrificial layer; depositing a top electrode on the second polymer-based layer; depositing a third polymer-based layer on the electrode such that the top electrode is between the second and third polymer-based layers; adhering the first and third polymer-based layers together such that the cavity is closed by the first and third polymer-based layers; and etching away the sacrificial layer such that the second polymer-based layer is released from the separate substrate.

The top electrode may be embedded within the second and third polymer-based layers.

The method may further comprise cross-linking the first and third polymer-based layers prior to adhering the first and third polymer layers together.

Patterning the first polymer-based layer and etching away the sacrificial layer may be performed using organic and non-toxic solvents.

The first polymer-based layer may be photosensitive, and patterning the first polymer-based layer to be the cavity may comprise: cross-linking a portion of the first polymer-based layer to remain following the etching by exposing the portion to ultraviolet radiation; and applying a photoresist developer to etch uncrossed-linked areas of the first polymer-based layer.

The second polymer-based layer may be thicker than the third polymer-based layer.

The second polymer-based layer may be at least five times thicker than the third polymer-based layer.

The relative thickness of the second polymer-based layer to the third polymer-based layer may be selected such that the top electrode resonates at a frequency of at least 1 MHz.

The fabrication may be performed at a temperature of no more than 150° C.

The substrate assembly may be flexible and bonded to a rigid carrier.

The top electrode may comprise a conductive polymer.

The substrate assembly may comprise an optically-transparent material.

The substrate assembly may further comprise an optically-transparent conductive bottom electrode on the substrate.

Adhering the first and third polymer layers together may comprise: treating surfaces of the first and third polymer layers to be adhered to each other with plasma; aligning the surfaces to each other; and pressing the surfaces together.

The adhering may be done in a bonding chamber at pressure of no more than 0.001 Torr.

The method may further comprise, after the adhering, trapping charge in the first polymer-based layer by: applying a voltage across the top electrode and the substrate assembly such that a portion of the first polymer-based layer contacting the top electrode is pulled into contact with the substrate assembly; maintaining the portion of the first polymer-based layer contacting the top electrode and the substrate assembly in contact for a period of time; and then ceasing applying the voltage.

The sacrificial layer may comprise a polymer.

Depositing the second polymer-based layer on the sacrificial layer may comprise completely covering the sacrificial layer with the second polymer-based layer.

The substrate assembly may comprise a conductive substrate.

The substrate assembly may comprise a non-conductive substrate and a conductive bottom electrode on the substrate.

Following the adhering a watertight seal may be around the cavity.

The sacrificial layer may be non-reactive when exposed to the second polymer-based layer and to a photoresist developer used during the patterning of the second polymer-based layer. The second polymer-based layer may be non-reactive when exposed to an etchant used to etch away the sacrificial layer.

The first, second, and third polymer-based layers may comprise SU8 photoresist.

The sacrificial layer may comprise an OmniCoat™ composition.

The cavity may have a height selected such that an operating voltage of the transducer is no more than 50 Volts.

The cavity may have a height of no more than 0.3 µm.

Depositing the sacrificial layer may comprise evaporating a composition that comprises a solvent, and then depositing the composition as the sacrificial layer. At least 70% and no more than 90% of the solvent may be evaporated.

According to another aspect, there is provided a capacitive micromachined ultrasound transducer, comprising: a substrate assembly that functions as a bottom electrode; a first polymer-based layer suspended above a sealed cavity between the first polymer-based layer and the substrate assembly; a second polymer-based layer placed on the first polymer-based layer; and a top electrode between the first and second polymer-based layers.

The top electrode may be embedded within the first and second polymer-based layers.

The second polymer layer may be thicker than the first polymer-based layer.

The second polymer-based layer may be at least five times thicker than the first polymer layer.

The cavity may have a height selected such that an operating voltage of the transducer is no more than 50 Volts.

The cavity may have a height of no more than 0.3 µm.

The cavity may be watertight.

The substrate assembly may comprise a conductive substrate.

The substrate assembly may comprise a non-conductive substrate and a conductive bottom electrode on the substrate.

The sacrificial layer may be non-reactive when exposed to the first and second polymer-based layers and to a photoresist developer used during the patterning of the first and second polymer-based layers. The first and second polymer-based layers may be non-reactive when exposed to an etchant used to etch away the sacrificial layer.

The first and second polymer-based layers may comprise SU8 photoresist.

The sacrificial layer may comprise an OmniCoat™ composition.

According to another aspect, there is provided a layered structure, comprising: a substrate assembly that functions as a bottom electrode; a first polymer-based layer suspended above a closed cavity between the first polymer-based layer and the substrate assembly; a second polymer-based layer placed on the first polymer-based layer; and a top electrode between the first and second polymer-based layers.

The top electrode may be embedded within the first and second polymer-based layers.

The second polymer layer may be thicker than the first polymer layer.

The second polymer layer may be at least five times thicker than the first polymer layer.

The cavity may have a height selected such that an operating voltage of the structure is no more than 50 Volts.

The cavity may have a height of no more than 0.3 µm.

The cavity may be watertight.

The substrate assembly may comprise a conductive substrate.

The substrate assembly may comprise a non-conductive substrate and a conductive bottom electrode on the substrate.

The sacrificial layer may be non-reactive when exposed to the second polymer-based layer and to a photoresist developer used during the patterning of the second polymer-based layer. The second polymer-based layer may be non-reactive when exposed to an etchant used to etch away the sacrificial layer.

The first and second polymer-based layers may comprise SU8 photoresist.

The sacrificial layer may comprise an OmniCoat™ composition.

This summary does not necessarily describe the entire scope of all aspects. Other aspects, features and advantages will be apparent to those of ordinary skill in the art upon review of the following description of specific embodiments.

BRIEF DESCRIPTION OF THE DRAWINGS

In the accompanying drawings, which illustrate one or more example embodiments:

FIGS. 32-37 depict perspective views sequentially arranged for illustrating operations comprising a method for fabricating a polymer-based CMUT, according to another example embodiment.

DETAILED DESCRIPTION

Figure 1:
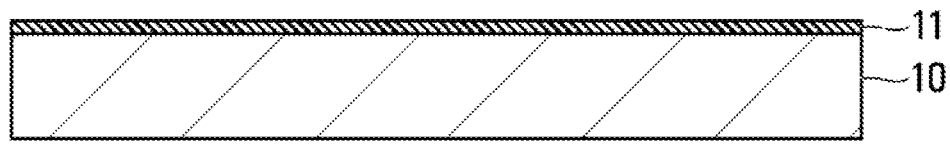
FIGS. 1-15 are schematic diagrams sequentially arranged for illustrating operations comprising a method for fabricating a polymer-based CMUT, according to one example embodiment.

In an ultrasound imaging system, ultrasonic waves emitted by a transducer travel along soft tissues, creating wave reflections (echoes) at the interfaces between tissues with different densities (e.g., fat and muscle); these echoes travel back to the transducer and are collected and processed to form an ultrasound image. The collection and manipulation of multiple echo signals along different directions is the basis of ultrasound image formation. Ultrasound transducers are a key component in an ultrasound imaging system, which transform electrical voltage into acoustic waves and vice versa.

Medical ultrasound systems have traditionally used piezoelectric materials for their transducers since the 1930s. Materials such as piezoelectric crystals (e.g., quartz), ceramics (e.g., lead zirconate titanate (PZT)), and thermoplastic fluoropolymers (e.g., polyvinylidene fluoride (PVDF)) have been used as the transducer materials. Despite the fact that piezoelectric transducers technology is mature, it suffers from many drawbacks such as the technical challenges in fabricating large two-dimensional arrays due to interconnect technologies and integration with electronics at the die-level.

Acoustic impedance (i.e., speed of sound in a material multiplied by its density, units: Rayls) is a measure of the opposition that a system presents to the acoustic flow resulting from an acoustic pressure applied to the system. It is an important figure in piezoelectric-based ultrasound systems since it determines their acoustic efficiency, which represents how much of the acoustic power is effectively transferred to tissues. An acoustic matching layer is typically used in biomedical piezoelectric-based systems to reduce the impedance mismatch between the crystals and tissues (30 MRayls to 1.5 MRayls); otherwise just a fraction of the acoustic power could be used. These matching layers are typically made of high-density rubber combined with liquid gel and are located between the crystals and the body.

Capacitive micromachined ultrasound transducers (CMUTs) are an alternative technology to conventional piezoelectric-based transducers. A CMUT may be modeled as a parallel-plate capacitor with a fixed electrode at bottom, a suspended membrane over a closed cavity, and another electrode patterned on top of the cavity. Ultrasound waves are generated when an AC signal superimposed on a DC voltage is applied between both electrodes; conversely ultrasound waves can be detected by measuring the variation in capacitance of the device while a DC voltage is applied in the presence of incoming ultrasound waves. The effective distance (i.e., thickness of the cavity and membrane) is preferably as small as possible for two reasons: 1) in order to maintain a low (e.g., less than 150 V) operating voltage during transmission (i.e., ultrasound waves generated from CMUT) and 2) to maintain a good sensitivity during reception (i.e., ultrasound waves arriving to the CMUT), since the capacitance variation is greater for large capacitance devices (i.e., those devices with comparatively thin dielectrics).

Silicon nitride and polysilicon are the most popular materials for membranes in conventional CMUTs fabrication, while metals such as aluminum or chromium are patterned on top of the membranes to become the top electrode. The membrane materials are chosen mainly because of their mechanical properties so the membranes can be as thin as possible in order to minimize the effective gap between the bottom and top (or "hot") electrodes.

By decreasing the effective gap between electrodes, the electric-field share of the gap and the capacitance increase, and the impedance matching to the electronics improves. Starting with a desired operational frequency and a specific limit for the biasing voltage, the CMUT membrane should be designed to be as thick as possible given the fact that its bandwidth linearly increases with its thickness.

In contrast to the above materials, photopolymers are inexpensive and can be patterned using UV light; their low density and high mechanical strength make the application of these polymers interesting in the ultrasound field mainly because acoustic impedance matching with the medium into which ultrasonic waves are sent and received can be greatly improved. Nonetheless the challenge in fabricating CMUTs using polymers is that a thick membrane with a metal electrode on top is needed to reach the MHz region, contravening the required short gap between electrodes for low operational voltages and maximum sensitivity. There has been some research in fabricating CMUTs using polymer materials; however, given their large membrane thickness the operational voltages were in the order of hundreds of volts, which is incompatible with biomedical ultrasound applications. Moreover, the mentioned devices are suitable operating in air only, and not for operating in conjunction with human tissues.

The embodiments described herein are directed at methods for fabricating a layered structure, such as a CMUT, and at that structure itself. In at least some example embodiments, surface micromachining may be used to fabricate the layered structure. When surface micromachining is used, a sacrificial layer is deposited on a substrate; the sacrificial layer is patterned into a first shape; a first polymer-based layer is deposited on the sacrificial layer; an electrode is deposited, on the first polymer-based layer, above the sacrificial layer; a second polymer-based layer is deposited on the electrode such that the electrode is between, and in some embodiments embedded, within the first and second polymer-based layers; and the sacrificial layer is then etched away to form a cavity under the electrode.

In at least some example embodiments in which surface micromachining is used to manufacture a CMUT, the sacrificial layer is deposited on to a substrate assembly that functions as a bottom electrode; the sacrificial layer is patterned to be shaped as a cavity of the CMUT; the first polymer-based layer is deposited on the sacrificial layer; a via hole is patterned through the first polymer-based layer to the sacrificial layer; a top electrode is patterned, above the sacrificial layer, on the first polymer-based layer; a second polymer-based layer is deposited on the top electrode such that the top electrode is embedded within the first and second polymer-based layers; the sacrificial layer is etched away, using the via hole, to form the cavity of the CMUT; and the cavity is closed.

In at least some different embodiments, wafer bonding may be used to fabricate the layered structure. When wafer bonding is used, a first polymer-based layer is deposited on a first substrate; the first polymer-based layer is patterned to be a cavity; a sacrificial layer is deposited on a second substrate; a second polymer-based layer is deposited over the sacrificial layer; an electrode is deposited on the second polymer-based layer; a third polymer-based layer is deposited on the electrode such that the electrode is between, and in some embodiments embedded, within the second and third polymer-based layers; the second and third polymer-based layers are cross-linked; the first and third polymer-based layers are adhered together such that the cavity is sealed by those layers; and the sacrificial layer is etched away such that the second polymer-based layer is released from the second substrate.

In at least some example embodiments in which wafer bonding is used to manufacture a CMUT, the first polymer-based layer is deposited on the substrate assembly, which functions as the bottom electrode; the first polymer-based layer is patterned to be a cavity of the CMUT; the sacrificial layer is deposited on a separate substrate; the second polymer-based layer is deposited over the sacrificial layer; the top electrode is deposited on the second polymer-based layer; the third polymer-based layer is deposited on the top electrode such that the top electrode is embedded within the second and third polymer-based layers; the first and third polymer-based layers are adhered together such that the cavity is closed; and the sacrificial layer is etched away such that the second polymer-based layer is released from the separate substrate.

As used herein, "embedding" an electrode with a polymer means completely covering the electrode with the polymer, except for any electrical connections made with that electrode.

Also as used herein, "patterning" a material means to selectively remove that material either directly (e.g., if it is photosensitive) or by using a masking layer (e.g., in the case of the OmniCoat™ composition, as discussed further below).

In at least some of the embodiments in which a polymer-based CMUT is fabricated, the polymer material may be inexpensive, easy to process, and be capable of being made in large arrays. Additionally, in contrast to conventional CMUTs, the top electrode is embedded within two polymer layers, with the bottom layer being thinner than the top layer; this, combined with forming a sufficiently thin CMUT cavity by etching away a sacrificial layer, permits the CMUT to reach the MHz operative region without requiring unacceptably high operating voltages.

A detailed description of the fabrication operations and relevant information about the materials used follows. FIG. 1 to FIG. 18 are schematic diagrams sequentially arranged for illustrating operations comprising a method for fabricating a polymer-based CMUT according to a surface micromachining embodiment. FIGS. 19-30 depict an analogous method according to a wafer bonding embodiment.

Surface Micromachining

Referring now to FIG. 1, there is shown a cross-sectional view of a substrate assembly in the form of an electrically conductive substrate 10 (an electrically conductive silicon wafer in this case). A low electrical resistance of this substrate 10 facilitates the substrate 10 acting as a bottom electrode in the finished CMUT. In some different embodiments (not depicted), a dedicated bottom electrode can be patterned over an insulating substrate 10 as an alternative. CMUTs are typically fabricated using silicon wafers as substrates, but any version of the rigid to semi-rigid surface with a smooth hydrophilic surface is sufficient to be used with this methodology. The surface of the substrate 10 is hydrophilic in at least some example embodiments in order to achieve a wet release of the final membrane described in subsequent operations.

A sacrificial layer 11 is deposited on the substrate 10 by spin coating. This sacrificial layer 11 will become the evacuated cavity 21 in the finished CMUT. The required thickness of the sacrificial layer 11 for a CMUT can range from a few hundreds of nanometers (nm) (e.g., 300 nm) to a couple of micrometers (µall) (e.g., 2 µm). A highly selective etchant is used to etch away the sacrificial layer 11 without damaging the CMUT's membranes, which are formed in subsequent operations as described below.

The OmniCoat™ composition by MicroChem Corp. has an excellent selectivity during etching and it enhances the adhesion of photoresists to different substrates. The two main chemical components in OmniCoat™ composition are cyclopentanone (a solvent that gets evaporated) and Propylene Glycol Monomethyl Ether (PGME). The OmniCoat™ composition also comprises a polymer (less than 1% of total volume) and a surfactant (also less than 1% of total volume). The OmniCoat™ composition is not photosensitive and its typical thickness during spin coating ranges from 5 nm to 15 nm, which limits its conventional use to releasing large structures by immersing them in developer for a few hours until the structures get released and float away from the carrying substrate. Still, this thickness range (5-15 nm) is well below the typical thickness used for sacrificial layers when conventional CMUTs are fabricated (200 nm-5,000 nm). In the depicted example embodiments, the OmniCoat™ composition is used for the sacrificial layer 11. In at least some example embodiments, the OmniCoat™ composition is evaporated prior to depositing it as the sacrificial layer 11. For example, evaporating a certain percentage of the solvents of the off-the-shelf OmniCoat™ composition (e.g., 85%) prior to its deposition allows a relatively thick sacrificial layer 11 (e.g., 0.3 µm), to be deposited in a single step. This may help to increase efficiency and to allow for greater precision in laying a sacrificial layer 11 of a desired thickness. In at least some other embodiments (not depicted), the OmniCoat™ composition may not be evaporated at all prior to its deposition as the sacrificial layer 11; for example, without any pre-deposition evaporation, multiple layers of the OmniCoat™ composition may be deposited in order to reach a desired thickness. In further additional embodiments (not depicted), while a certain proportion of its solvents may be evaporated, that proportion may be more or less than 85%. For example, if a thinner sacrificial layer 11 is desired, then a smaller percentage (e.g., 70%) of the solvents in the OmniCoat™ composition may be evaporated; alternatively, more (e.g., 90%) of the solvents may be evaporated. More generally, this pre-deposition evaporation may be performed on whatever composition is used as the sacrificial layer 11.

The sacrificial layer 11 is patterned to create the areas that will become the cavity 21 (shown in FIG. 15) in the final device as well as releasing channels to permit access to this cavity 21. Given the fact that the OmniCoat™ composition is not photosensitive it cannot be directly patterned and needs to be removed indirectly.

Figure 2:
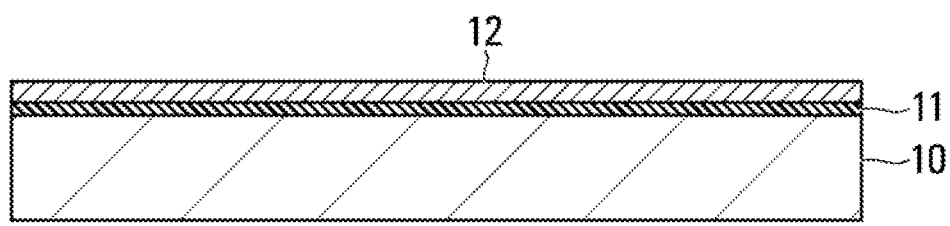

Referring now to FIG. 2, a layer of positive photoresist (PR) 12 is deposited on top of the sacrificial layer 11. This photoresist (S1813) is selected so that its developer dissolves the cross-linked photoresist 13 (shown in FIG. 3), which results after ultraviolet light (UV) exposure as well as the sacrificial material 11.

Figure 3:
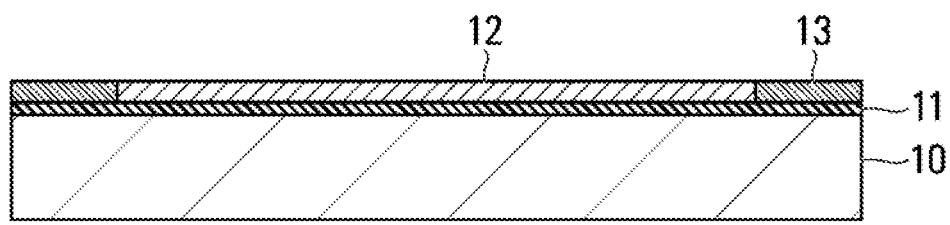

Referring now to FIG. 3, the photoresist layer 12 is exposed to UV using a photomask and a mask aligner. The areas exposed to UV become cross-linked photoresist 13 and the areas not exposed to UV are left intact (uncross-linked).

Figure 4:
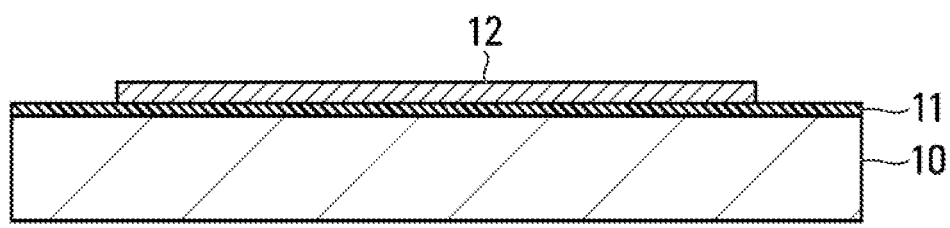

Referring now to FIG. 4, the cross-linked photoresist 13 is etched away (removed) by placing the sample in an aqueous solution containing an alkaline-based photoresist developer (MF319). The photoresist 12 that is uncross-linked remains intact.

Figure 5:
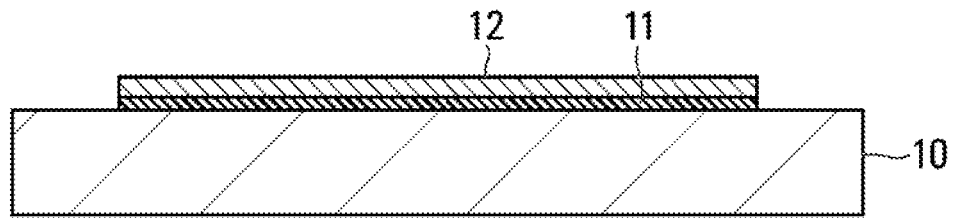

Referring now to FIG. 5, while the sample is still in the photoresist developer (MF319) from FIG. 4, the etching continues and starts dissolving the sacrificial layer 11. The patterned photoresist layer 12 acts as a masking layer to protect the sacrificial layer 11 underneath. The etching is stopped as soon as the sacrificial layer 11 under the cross-linked photoresist 13 is removed, leaving the substrate 10 exposed for subsequent operations.

Figure 6:
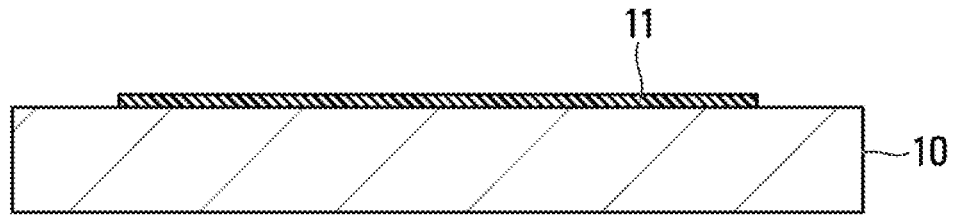

Referring now to FIG. 6, the masking layer of positive photoresist 12 is removed by immersing the sample in acetone or any other solvent suitable to dissolve the positive PR 12 without damaging the sacrificial layer 11. The sacrificial layer 11 offers an excellent selectivity (chemical resistance) to the solvent used (acetone). What is left behind is a patterned sacrificial layer 11 containing the areas that will become the cavity 21 in the final device as well as the etch channels.

Figure 7:
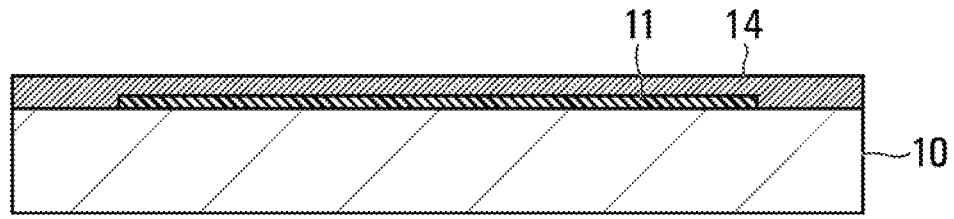

Referring now to FIG. 7, a first polymer-based layer 14 comprising a negative photosensitive polymer-based material (SU8 photoresist, hereinafter interchangeably referred to simply as "SU8") 14 is deposited, conformally covering the sacrificial layer 11. The thickness of the layer 14 is designed to be as thin as possible to conformally coat the sacrificial layer 11 and to be able to maintain good electrical insulation between the conductive substrate 10, which acts at the finished CMUT's bottom electrode, and a top electrode 16 (shown in FIGS. 10-15). The SU8 comprises Bisphenol A Novolac epoxy dissolved in an organic solvent, and comprises up to 10 wt % Triarylsulfonium/hexafluoroantimonate salt; in different example embodiments (not depicted), the polymer-based material may have a different composition. The SU8 is also optically transparent, which facilitates inspection of the finished device. In at least some different embodiments, a material may be used in place of the SU8, and that replacement material may be non-opaque (i.e., partially or entirely transparent).

The layer 14 in at least the depicted example embodiment comprises a photopolymer. Photopolymers are inexpensive and can be patterned using UV; their low density and high mechanical strength make the application of these polymers interesting in the ultrasound field mainly because the impedance matching with the medium into which ultrasonic waves are transmitted and from which reflected waves are received can be greatly improved. Nonetheless the challenge in fabricating CMUTs using polymers is that, conventionally, a thick membrane with a metal electrode on top is needed to reach the MHz operational region, contravening the required short gap between electrodes that facilitate low operational voltages and maximum sensitivity.

Figure 8:
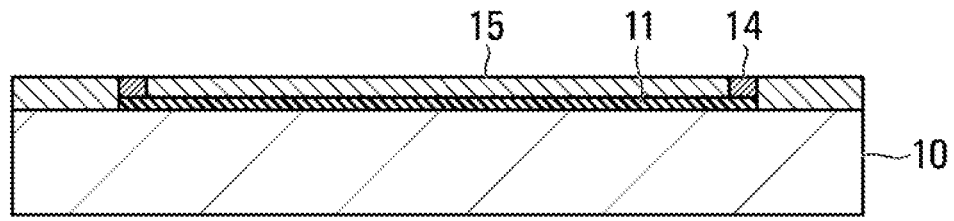

Referring now to FIG. 8, the layer 14 is exposed to UV using a photomask and a mask aligner. The areas exposed to UV light become cross-linked areas 15 of the layer 14 and the areas not exposed to UV are left as uncross-linked areas.

Figure 9:
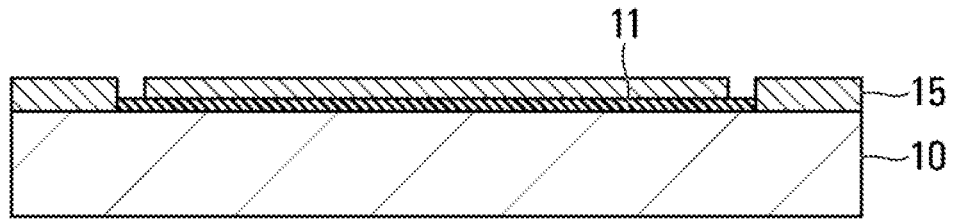

Referring now to FIG. 9, the uncross-linked areas of the first polymer-based layer 14 are etched away (removed) by placing the sample in an aqueous solution containing a negative photoresist developer (SU8 developer). The cross-linked areas 15 remain intact.

Figure 10:
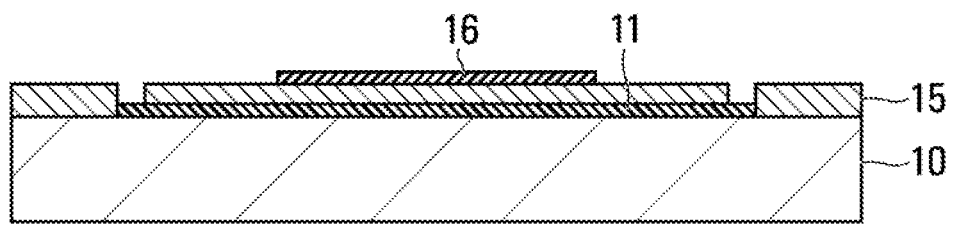

Referring now to FIG. 10, an electrically conductive top electrode (chromium) 16 is patterned on top of the cross-linked areas 15 of the first polymer-based layer 14 using lift-off methods. This electrode 16 is in at least some example embodiments made as thin as possible without sacrificing electrical conductivity in order to not greatly modify the structural properties of the cross-linked areas 15, which will later become the membrane of the finished device.

The material for this electrode 16 in at least the depicted example embodiment is typically metallic; nevertheless any other material capable of fulfilling the functions of the top electrode 16 can be used (e.g., conductive polymers, optically transparent materials, etc.). A good adhesion between this top electrode 16 and the cross-linked areas 15 is present in order to avoid any potential delamination during normal operation of the finished device. Using chromium as the top electrode 16 when the cross-linked areas 15 comprise SU8 may help to facilitate adhesion.

At this point the overall thickness of the membrane (i.e., the cross-linked areas 15 and the top electrode 16) is thin compared to its diameter so that its resonant frequency would be just a fraction of the desired operational frequency in the finished device. A much thicker membrane is required in order to reach the desired operational frequency in, for example, the MHz range.

Figure 11:
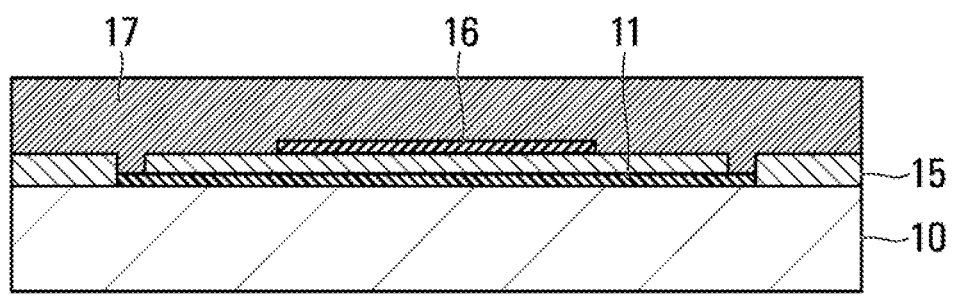

Referring now to FIG. 11, a second polymer-based layer 17 is deposited over the membrane, conformally coating the sacrificial layer 11, the first polymer-based layer 15, and the top electrode 16. The second polymer-based layer 17 is of the same photosensitive polymer (SU8) as the first polymer-based layer 14 in at least the depicted example embodiment; however, in different embodiments (not depicted) the layers 14,17 may comprise different polymers. The thickness of this second polymer-based layer 17 is designed to be a few times (~5) thicker than that of the cross-linked areas 15 of the first polymer-based layer 14.

Figure 12:
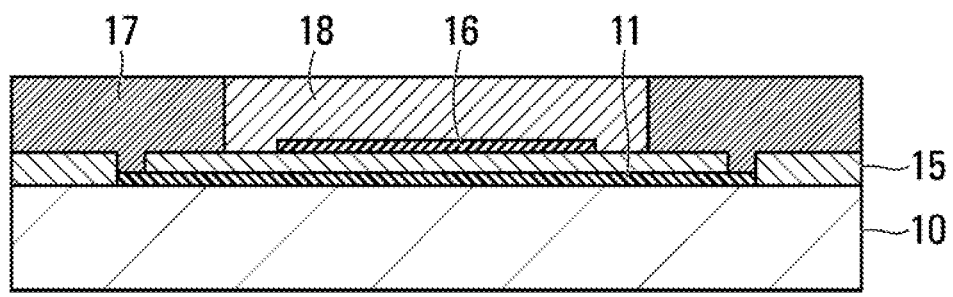

Referring now to FIG. 12, following the same process as described in respect of FIG. 8, the second polymer-based layer 17 is exposed to UV using a photomask and a mask aligner. The areas exposed to UV light become cross-linked areas 18 and the areas not exposed to UV are left intact (uncross-linked).

Figure 13:
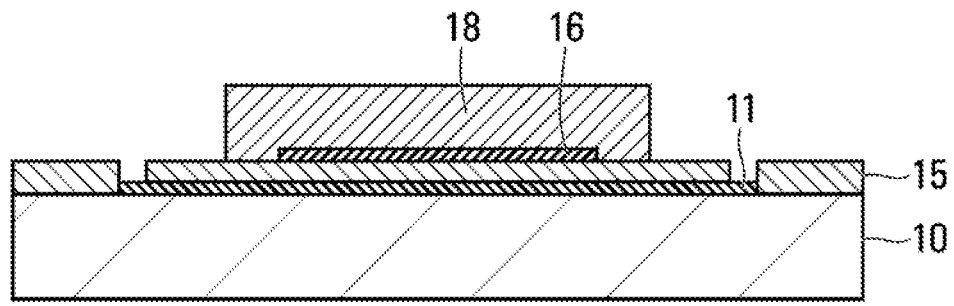

Referring now to FIG. 13, the uncross-linked areas of the second polymer-based layer 17 are etched away (removed) by placing the sample in an aqueous solution containing a negative photoresist developer (SU8 developer). The cross-linked areas 18 remain intact.

At this point, the top electrode 16 becomes embedded between the cross-linked areas 15,18 of the two polymer-based layers 14,17. The advantage of this approach is that the membrane is still able to operate in the MHz region because of the added thickness from the second polymer-based layer 17, which increases the effective stiffness while still maintaining a low operational voltage thanks to the small effective distance between the bottom substrate 10 and the embedded top electrode 16.

This fabrication process is not limited to the operation in the MHz range for biomedical ultrasound imaging. If desired, the same or an analogous fabrication process can be used to obtain membranes that operate in the Hz and kHz region for air-coupled operation applications, for example. The final operational frequency of the membrane depends on the geometry of the cell. This means that membranes that resonate at different frequencies can be operated with very similar voltages. For example, two membranes with the same diameter can operate with the same voltage (same effective distance between electrodes), but one can be thinner for lower frequencies and the other ticker for high-frequency operation.

Figure 14:
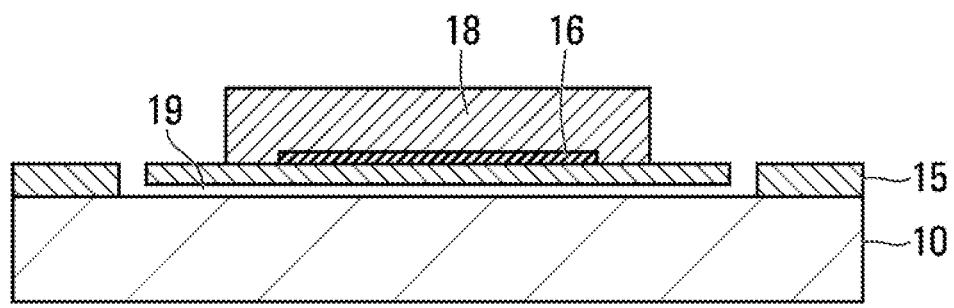

Referring now to FIG. 14, the sample is then immersed in an aqueous alkaline-based solution containing the etchant (MF319) of the sacrificial layer 11. The patterned sacrificial layer 11 is gradually removed though via holes and etch channels until it is fully dissolved. At this point the etchant is replaced by water and then by isopropanol (IPA). A critical point dryer system is used to release the membrane, avoiding stiction problems and remaining with a membrane suspended above an un-sealed cavity 19.

Figure 15:
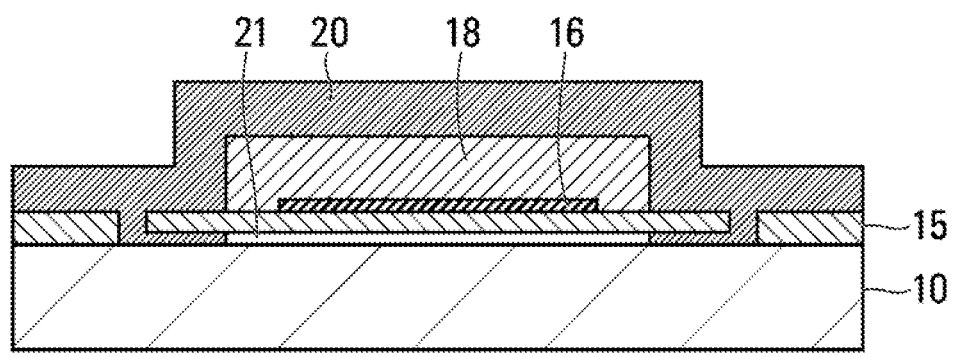

Referring now to FIG. 15, the sample is encapsulated by a bio-compatible material 20 (a poly(p-xylylene) polymer, such as parylene) inside a low-pressure chamber; while various pressures may be used, in the depicted example embodiment the pressure within the chamber is $1 \times 10^{-3}$ Torr. The encapsulating material 20 conformally coats the entire sample, sealing the via holes and etch channels to form a closed cavity 21. In at least the depicted example embodiment, the cavity 21 is vacuum sealed and is watertight and airtight, which helps to avoid squeeze-film effects and to reduce the risk of voltage breakdown. In different example embodiments, the cavity 21 may not be vacuum sealed, or may be watertight and not airtight.

At this point the fabrication process is complete and the finished device (i.e., the CMUT) results. Any electrical interconnection is made before this step as the biocompatible material (parylene) is an excellent electrical insulator and is safe for use on humans.

This fabrication process may use optically transparent or semi-transparent materials for any one or more of the substrate (e.g. glass or quartz), for the electrodes (e.g. Indium oxide, which is semi-transparent) and for the sealing layer (parylene). This leads to an optically transparent or semi-transparent transducer.

Figure 16:
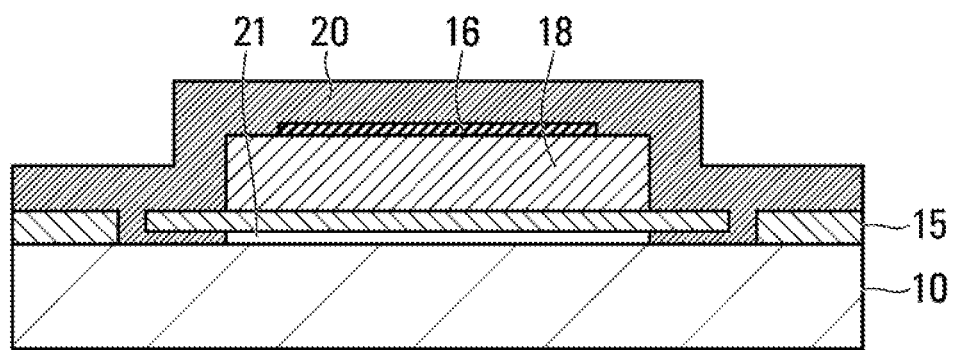
FIG. 16 depicts a schematic diagram of a CMUT in contrast with the embodiment depicted in FIGS. 1-15.

In the CMUT depicted in FIG. 15, the cross-linked areas 15 of the first polymer-based layer 14 is significantly thinner than the cross-linked areas 18 of the second polymer-based layer 17. FIG. 16 depicts an example CMUT in which the electrode 16 is located above the second polymer-based layer 18 and then encapsulated by the encapsulating material 20.

The operating voltage of the CMUT of FIG. 15 is much lower than that of FIG. 16. For instance, the resonant frequency of the membranes in FIG. 15 and FIG. 16 is the same since all the materials and thickness remain the same except for the location of the top electrode. The operational voltage of the CMUT shown in FIG. 15 is 50 Volts, whereas the operational voltage of the CMUT shown in FIG. 16 is 300 Volts, which is prohibitive in medical ultrasound systems.

Figure 17:
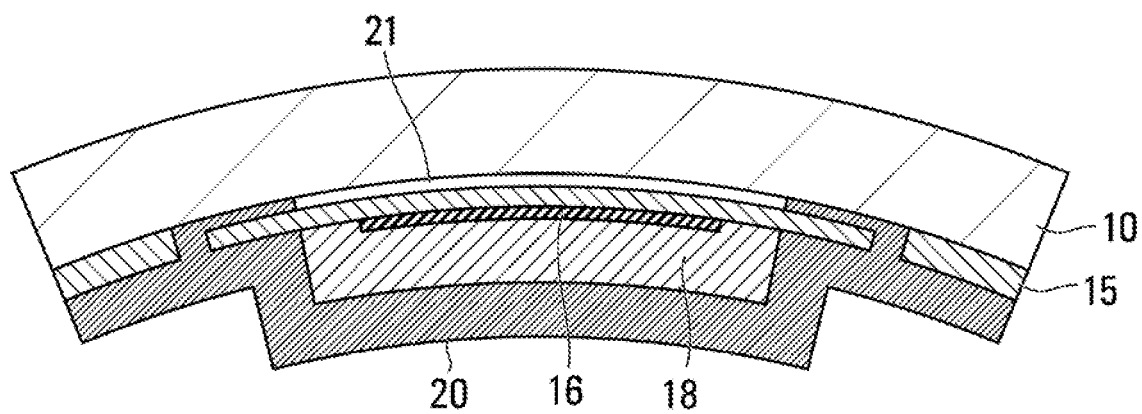
FIGS. 17 and 18 depict schematic diagrams of curved polymer-based CMUTs, according to additional example embodiments.
Figure 18:
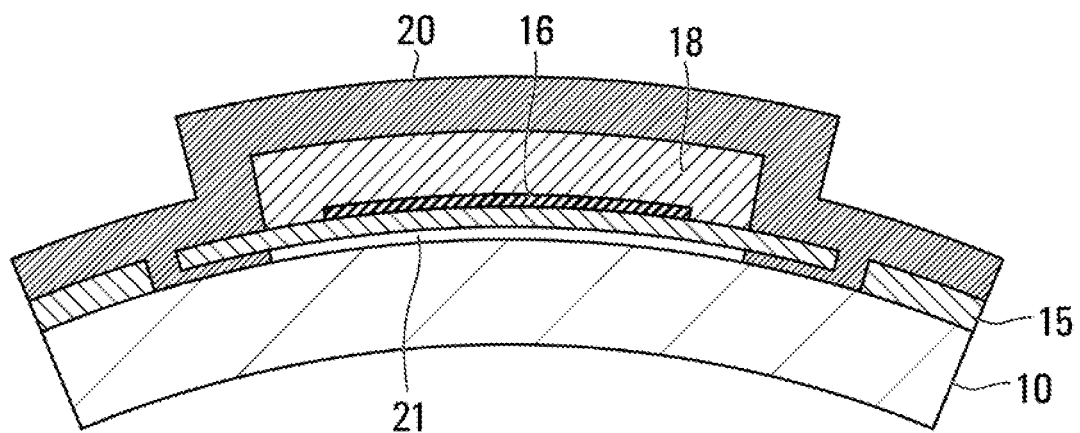

The described materials and fabrication process of FIGS. 1-15 may be used to fabricate the CMUT on flexible substrates. This is an advantage for conformal imaging systems in which the ultrasound elements are to be curved around different parts of the human body as depicted in FIG. 17 and FIG. 18. The polymer materials used for fabrication are sufficiently flexible, allowing the CMUT to bend around small radii of curvature without sacrificing performance or mechanical stability.

Traditional CMUTs fabricated with polysilicon and silicon nitride are generally inflexible and employ hazardous chemicals (potassium hydroxide and hydrochloric acid) during etching. The chemicals may present a risk for people working with these materials as they are corrosive and the vapours can cause internal organ damage, resulting in severe and in some cases fatal consequences. The fabrication operations according to at least some of the example embodiments herein can be performed in simple low-cost and safe fabrication facility.

The aforementioned fabrication process in at least some example embodiments employ non-hazardous materials, i.e. only organic solvents are used during fabrication (acetone, isopropanol, SU8 developer, and positive photoresist developer). The health risks associated with an accidental prolonged exposure to these materials are generally limited to drowsiness and minor skin irritation. The etchant used to remove the OmniCoat™ composition (MF319 or Tetramethylammonium hydroxide diluted in water) can be safely disposed of in ordinary laboratory drain systems when diluted in water as it is considered a mild base.

The fabrication costs associated with the fabrication process depicted in FIGS. 1-15 is significantly less than the cost required to manufacture conventional designs. As of December, 2017, the estimated material costs to fabricate an array of ultrasound transducers is less than US$100 inside a university laboratory, with a potential cost reduction if mass produced; meaning that the fabricated devices can be considered at some point disposable.

The maximum temperature required to manufacture CMUTs using the described process in FIGS. 1-15 for this process is 150° C., consequently requiring minimal thermal protection systems and using minimal thermal budget compared to conventional fabrication processes using polysilicon.

Additionally, using polymers as structural material for CMUTs means that if an acoustic matching layer is required it can be manufactured using the same kind of polymer materials with embedded fillers.

Referring now to FIGS. 32-37, there are depicted perspective views sequentially arranged for illustrating operations comprising a method for fabricating a polymer-based CMUT, according to another example embodiment.

Referring now to FIG. 32, the electrically-conductive substrate 10 (e.g., silicon wafer) is uniformly coated with a sacrificial material (e.g., the OmniCoat' composition) and baked to form the sacrificial layer 11. A layer of positive photoresist (S1813) is deposited on top of the OmniCoat™ composition and baked. The sample is selectively exposed to UV to pattern the sacrificial layer 11's design. The sample is immersed in positive photoresist developer (MF319). The developer dissolves both unexposed areas in S1813 and the OmniCoat™ composition underneath, thereby leaving a patterned design of the sacrificial layer 11. The sacrificial layer 11 comprises an area to eventually form the CMUT cavity 21 as well as etch channels 37 and etch via holes 35.

Referring now to FIG. 33, the sample coated with the first polymer-based layer 14 comprising a polymer-based material (SU8), conformally covering the sacrificial layer 11. The thickness of the layer 14 is by design selected to be as thin as possible as long as the sacrificial layer 14 is covered and the breakdown voltage of the polymer exceeds the desired operational voltage. The sample is exposed to UV to pattern the anchor points of the sample as well as the first layer of the membrane. The sample is baked and developed in SU8 developer, leaving open windows for the etch channels 37.

Referring now to FIG. 34, the electrically conductive electrode 16 (chromium) is patterned on top of the first polymer-based layer 14 using lift-off micromachining methods; electrical connections 39 to the electrode 16 are concurrently patterned. The thickness of the electrode 16 is as thin as possible as long as a low resistance path is maintained. In at least some different embodiments (not depicted), the electrode 16 may comprise non-metallic materials, such as one or more conductive polymers.

Referring now to FIG. 35, the second polymer-based layer 17 is conformally coated on top of the electrode 16, covering the stack comprising the sacrificial layer 11, first polymer-based layer 14, and metal electrode 16. The second polymer-based layer 17 also comprises the SU8. The sample is exposed to UV to pattern the CMUT membrane and leave open areas for the via holes 35 on the first polymer-based layer 14. The purpose of this second polymer-based layer 17 is to increase the effective thickness of the membrane and therefore increase its resonant frequency. Electrical contacts are exposed to air. In the depicted example embodiment, only the areas corresponding to where the cavity 21 will be located in the finished CMUT is patterned with the second polymer-based layer 17; in different embodiments (not depicted), more than these areas may be patterned with the second polymer-based layer 17.

Referring now to FIG. 36, the sample is immersed in positive photoresist developer (MF319, same etching chemical as for the OmniCoat™ composition). Developer removes the sacrificial material through the via holes 35 and etch channels 37. The developer (MF319) is replaced by water and then by isopropyl alcohol (IPA) in a wet environment. The sample is immersed in IPA inside a critical point dryer system to release the membrane. Liquid $CO_2$ replaces IPA in a high-pressure environment and then the liquid $CO_2$ is converted to gaseous $CO_2$. At this point the membrane is suspended on the cavity 19. While a critical point system is used in the fabrication depicted in FIGS. 32-37, in different embodiments (not depicted) it may be omitted, particularly if the CMUT membrane is not prone to stiction given its dimensions.

Referring now to FIG. 37, the sample is placed in a low-pressure chamber (e.g., operated at $1 \times 10^{-3}$ Torr) and conformally coated with the encapsulating material 20 comprising polymer materials (parylene) so that the cavity 21 is vacuum-sealed (i.e., airtight) and watertight. The parylene's thickness is selected so the mechanical properties of the encapsulating material 20 in the finished CMUT are very similar (and in some embodiments identical) to the SU8 (e.g., in terms of density and Young's modulus); accordingly, in at least some embodiments the collective thickness of the encapsulating material 20 and the second polymer-based layer 17 are considered when comparing that thickness to that of the first polymer-based layer 15, the ratio of which influences the finished CMUT's operational frequency. The encapsulating material 20 seals the via holes 35 and etch channels 37, leaving a vacuum-sealed and watertight cavity once the sample is removed from the low-pressure chamber. Areas for electrical interconnections are protected prior this sealing step.

The resulting finished CMUT is a sealed CMUT element with a low pull-in voltage given its small effective separation between electrodes. The carrying substrate need not be limited to rigid materials; flexible material temporarily attached to a rigid carrier may be used as well. The sample may be electrically interconnected to an interface circuit prior to sealing (FIG. 36). An acceptable adhesion between polymer material and electrode is used to avoid mechanical failure during operation.

Wafer Bonding

In at least some example embodiments, wafer bonding technology can be used to manufacture a similar version of the CMUT depicted in FIG. 15. In this approach, the materials are deposited and processed in two separate substrates, such as silicon wafers. The materials deposited on the separate substrates are then adhered together and further processed to obtain CMUTs. The detailed fabrication description follows.

Figure 19:
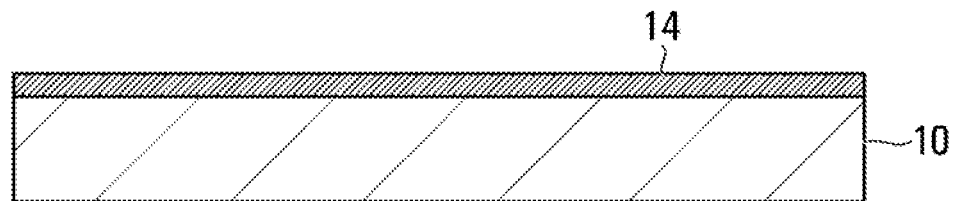
FIGS. 19-30 are schematic diagrams sequentially arranged for illustrating operations comprising a method for fabricating a polymer-based CMUT, according to another example embodiment.

Referring now to FIG. 19, the first polymer-based layer 14 comprising a polymer-based material (SU8) is deposited on top of a substrate assembly comprising the bottom substrate 10, which acts as the bottom electrode in the finished CMUT and which in the depicted example embodiment is electrically conductive.

Figure 20:
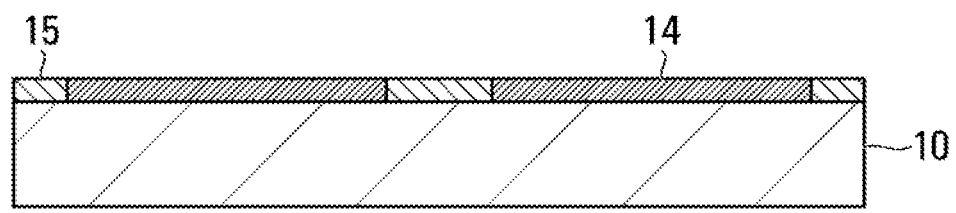

Referring now to FIG. 20, the first polymer-based layer 14 is exposed to UV using a photomask. The areas exposed to UV become the cross-linked areas 15 and the areas not exposed to UV are left uncross-linked.

Figure 21:
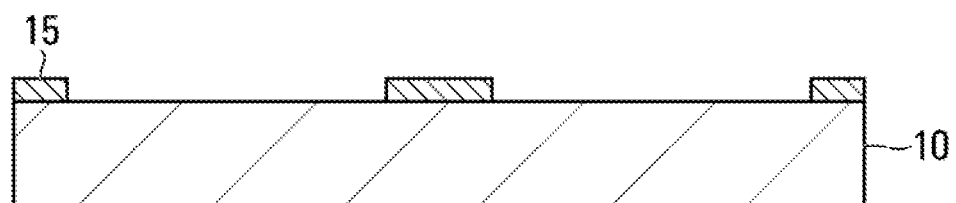

Referring now to FIG. 21, the uncross-linked areas of the first polymer-based layer 14 are etched away (removed) using photoresist developer (SU8 developer). The cross-linked areas 15 remain intact. The cross-linked areas 15 that remain following etching will act as pillars supporting the CMUT membranes.

Figure 22:
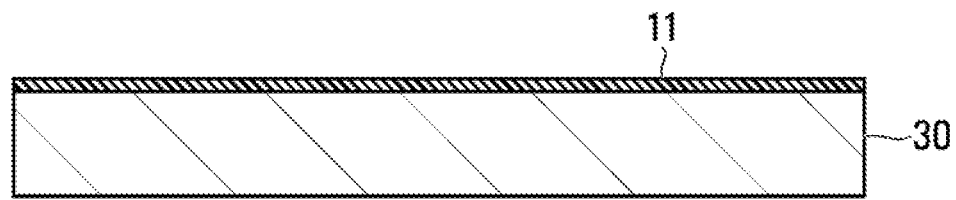

Referring now to FIG. 22, in a separate substrate 30 (silicon wafer or any other rigid and smooth substrate) a sacrificial layer 11 is deposited on top by spin coating. This sacrificial layer 11 will be used to release the separate substrate 30 following adhering, as discussed further below.

Figure 23:
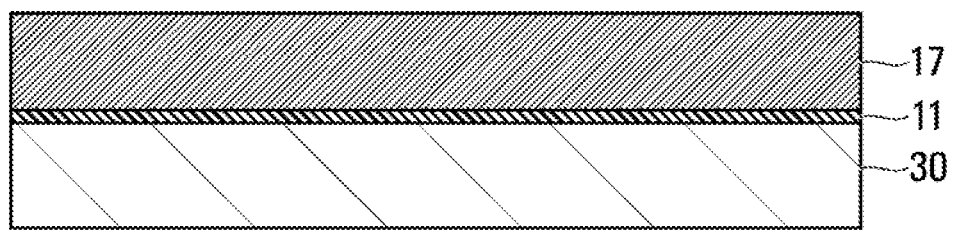

Referring now to FIG. 23, the second polymer-based layer 17, which in the depicted example embodiment comprises the same photosensitive polymer (SU8) as used for the first polymer-based layer 14, is deposited on top of the sacrificial layer 11; this layer 17 will become the top part of the finished CMUT.

Figure 24:
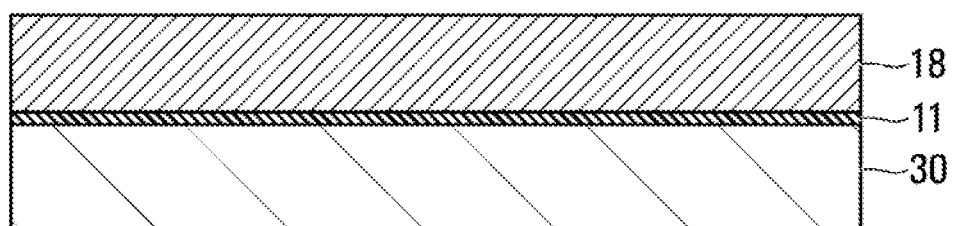

Referring now to FIG. 24, the second polymer-based layer 17 is exposed to UV using a photomask and a mask aligner. The areas exposed to UV become the cross-linked areas 18.

Figure 25:
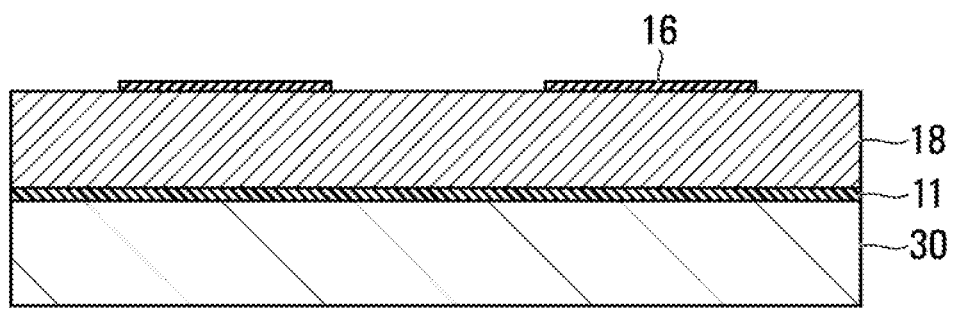

Referring now to FIG. 25, the electrically conductive top electrode 16 (chromium) is patterned on top of the cross-linked areas 18 using lift-off methods.

Figure 26:
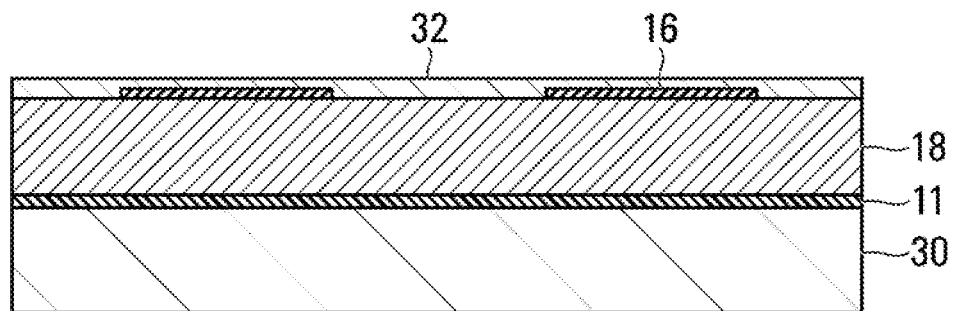

Referring now to FIG. 26, a third polymer-based layer 32 of the same photosensitive polymer (SU8) comprising the first and second polymer-based layers 14,17 is deposited on the top electrodes 16, conformally coating the metal electrodes 16 and the cross-linked areas 18 of the second polymer-based layer 17. At this point, the top electrode 16 becomes encapsulated between the cross-linked areas 18 of the second polymer-based layer 17 and the third polymer-based layer 32.

Figure 27:
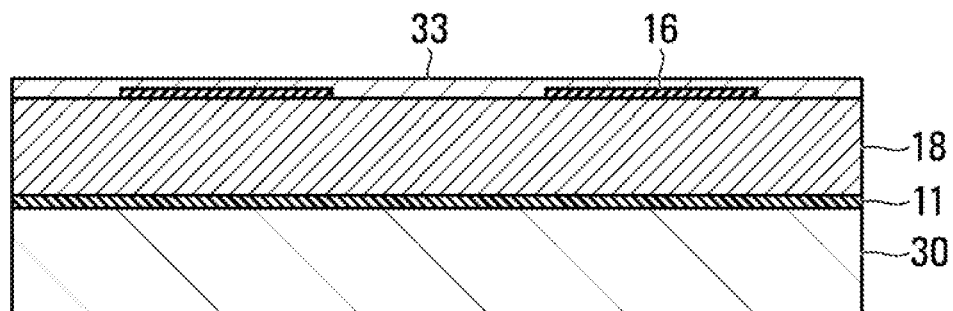

Referring now to FIG. 27, the third polymer-based layer 32 is exposed to UV using a photomask and a mask aligner. The areas exposed to UV become cross-linked areas 33. The purpose of the cross-linked areas 33 is to act as dielectric layer between the two electrodes (the bottom substrate 10 and the top electrode 16) in the finished CMUT. Cross-linking the first and third polymer-based layers 14,32 serves to promote adhesion between those layers; in at least some different example embodiments (not depicted), the cross-linking may be skipped if the layers 14,32 can be suitably adhered to each other without cross-linking.

Figure 28:
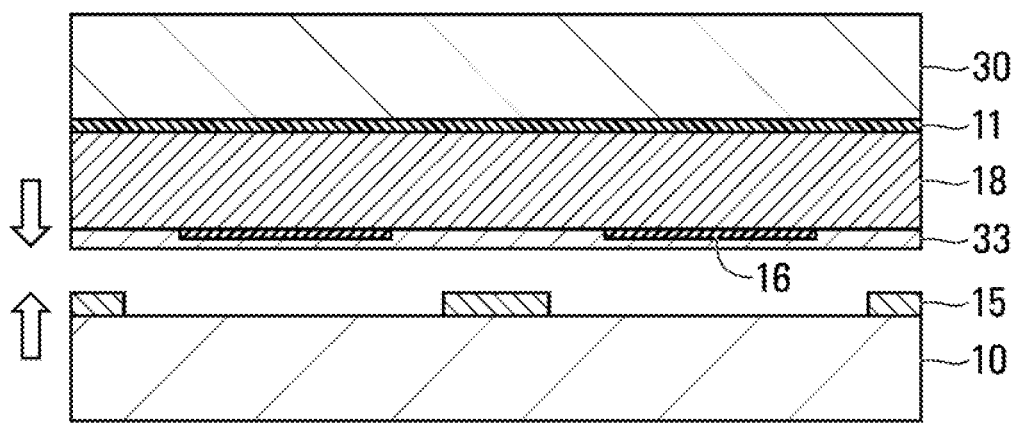

Referring now to FIG. 28, the surfaces of the separate samples as shown in FIG. 21 and FIG. 27 are treated with oxygen plasma, which allows the surfaces of both samples to be permanently adhered. The samples are aligned and placed face to face in a vacuum environment and pressed against each other. The vacuum may be any suitable pressure, such as $1 \times 10^{-3}$ Torr as described above in the surface micromachining embodiment. In different embodiments (not depicted), the samples may not be treated with oxygen plasma.

Figure 29:
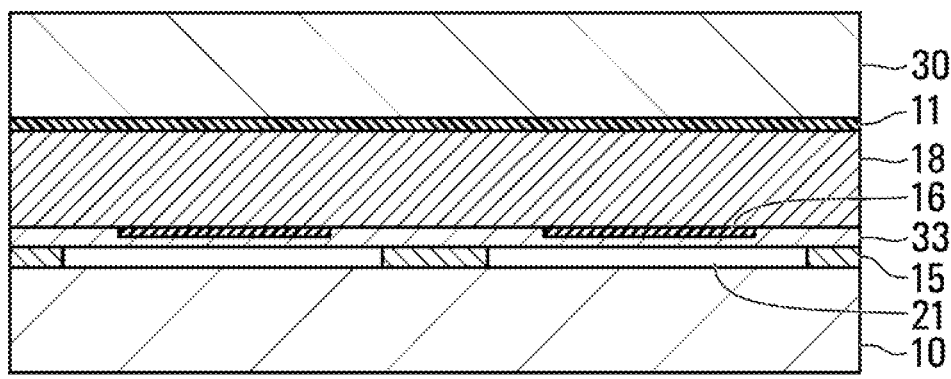

Referring now to FIG. 29, after releasing the pressure both samples are now permanently attached, creating an array of vacuum-sealed cavities 21.

Figure 30:
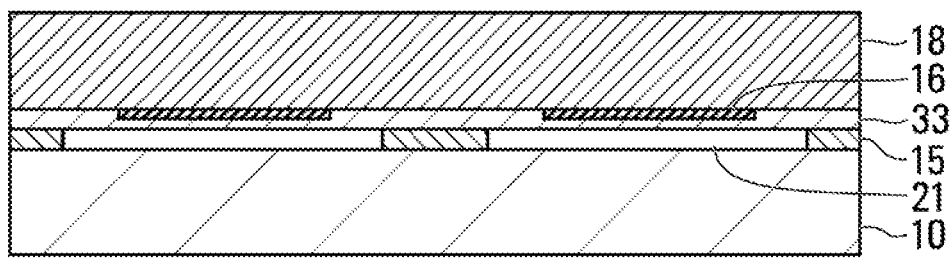

Referring now to FIG. 30, the sample is immersed in an aqueous alkaline-based solution containing the etchant (MF319) of the sacrificial layer 11. The sacrificial layer 11 is gradually removed until the separate substrate 30 is released. This etchant does not attack the polymer not the metallic materials used. At this point the fabrication process is complete and the device becomes watertight. As with the surface micromachining embodiment of FIGS. 1-15, in certain embodiments the cavities 21, while closed, may not be airtight or watertight; in other embodiments, the cavities 21 may be watertight and not airtight.

The CMUT fabricated using wafer bonding does not comprise the encapsulating material 20 in the depicted example embodiments as the cavities 21 are vacuum-sealed following adhesion. This simplifies fabrication.

The fill factor (number of CMUTs per unit area) may be improved using wafer bonding vs. surface micromachining, as the CMUTs can be placed closer to each another since the releasing holes (vias) and channels do not exist. By using hexagonal or square membranes the fill factor can be increased, relative to circular membranes.

In at least some example embodiments, Roll-to-Roll (R2R) technology may be applied to fabricate the cavity 21.

In the wafer bonding embodiment, one or both of the substrates 10,30 may be flexible if bonded to a rigid carrier.

Charge Trapping

Charge trapping effects in CMUTs may be observed, for example, when a zero-bias resonator is fabricated by purposely trapping electrical charges in a dielectric layer by applying a large bias voltage beyond pull-in. More generally, charge trappings effects may be observed for any resonator (including a CMUT) or layered device fabricated according to the embodiments described herein, including those that are not zero-bias. In the examples described herein, the trapped charging effect contributes positive to the normal operation of the resonator (e.g., a materially lower operational voltage may be used when trapped charges are present).

Figure 31:
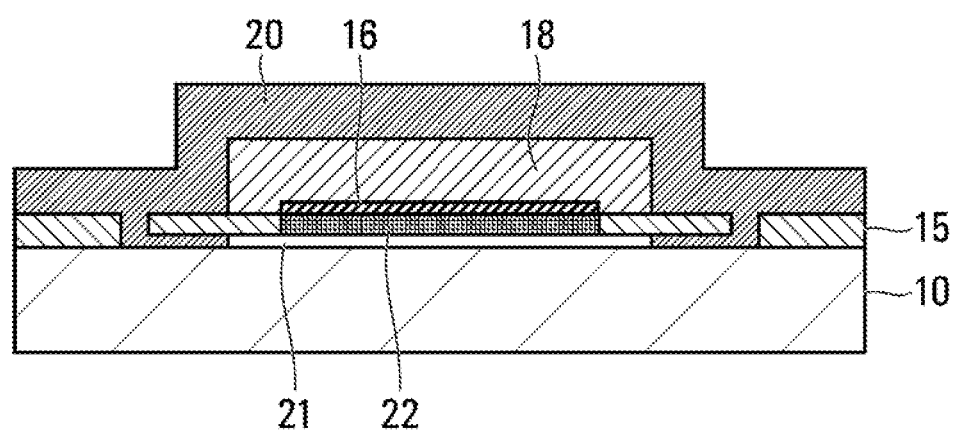
FIG. 31 depicts a schematic diagram of a polymer-based CMUT subject to charge trapping effects, according to another example embodiment.

Referring now to FIG. 31, electrical charges get trapped in the SU8 membrane underlying the top electrode 16 of the CMUT of, for example, FIG. 15 or 30, when a DC voltage larger than pull in (VPI=65V) is applied between the top electrode 16 and the bottom substrate 10, which acts as the bottom electrode. This causes the membrane to collapse (e.g., to be pulled into contact with the substrate 10), resulting in the electrical field acting on the membrane to increase. In at least some different example embodiments (not depicted) the cavity 21 is sufficiently tall that the membrane does not contact the bottom substrate 10 when the DC voltage is applied. After removing the DC voltage, the membrane returns to its initial position having electrical charges 22 trapped in the dielectric film (SU8).

The electrical charges 22 trapped in the membrane contribute to the electrostatic force during operation (acting like a built-in voltage), meaning that a lower DC bias voltage may be used to bring the membrane closer to the bottom substrate 10.

It has been experimentally shown that the electrical charges 22 get trapped in the volume of the SU8 film (in theory, by the molecules' dipole alignment) and not on the metal electrode 16 (as an ordinary capacitor). This prevents the CMUT from getting "discharged" even if its terminals are shorted.

Experimental Results

Figure 38:
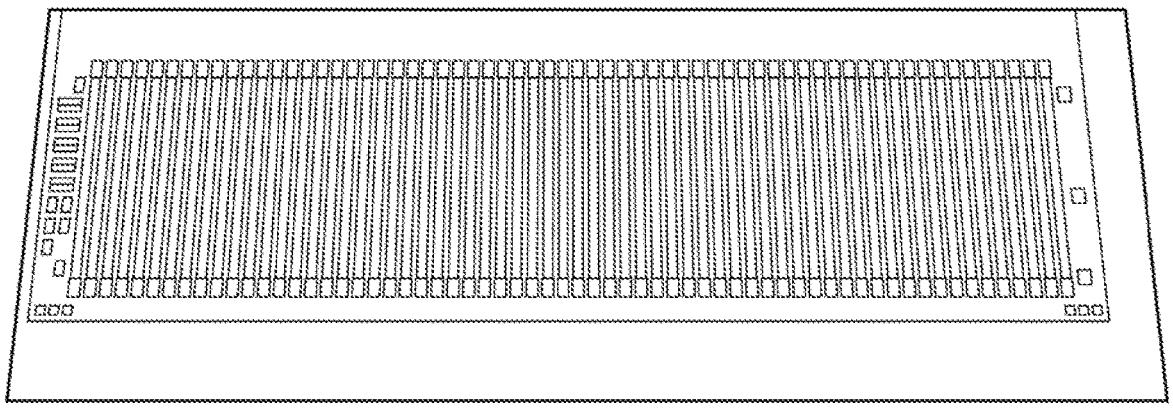
FIGS. 38-44 depict experimental data relating to CMUTs fabricated according to the example embodiment of FIGS. 1-15.
Figure 39:
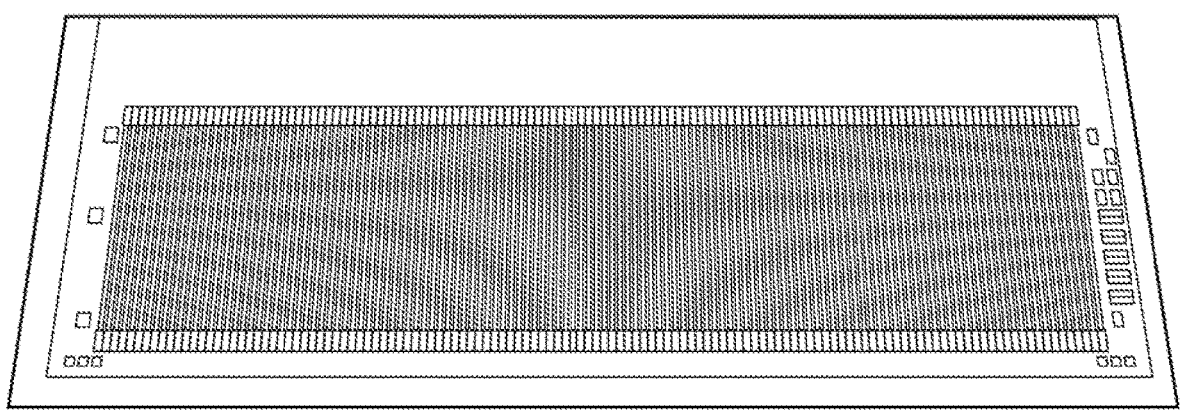

Using the surface micromachining embodiment described in respect of FIGS. 1-15, a set of linear arrays containing 64 and 128 CMUT elements, with each element comprising an interconnected matrix of CMUT cells sharing a common bottom electrode in the form of a conductive substrate 10 (a silicon wafer), were fabricated. These CMUT elements are shown in FIG. 38 (64 elements) and FIG. 39 (128 elements). The total fabrication time was 16 Hrs.

Figure 41:
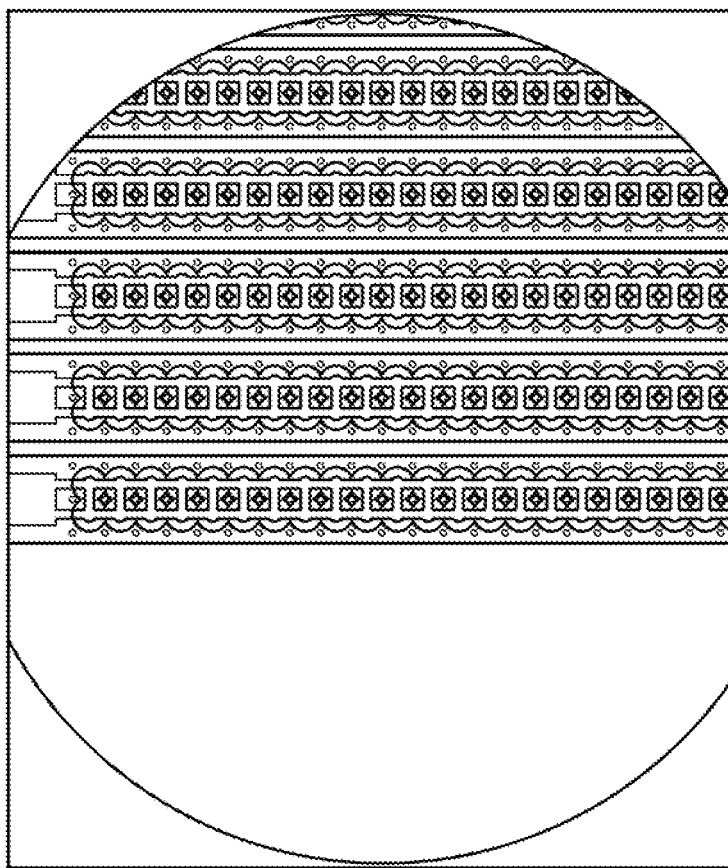
Figure 40:
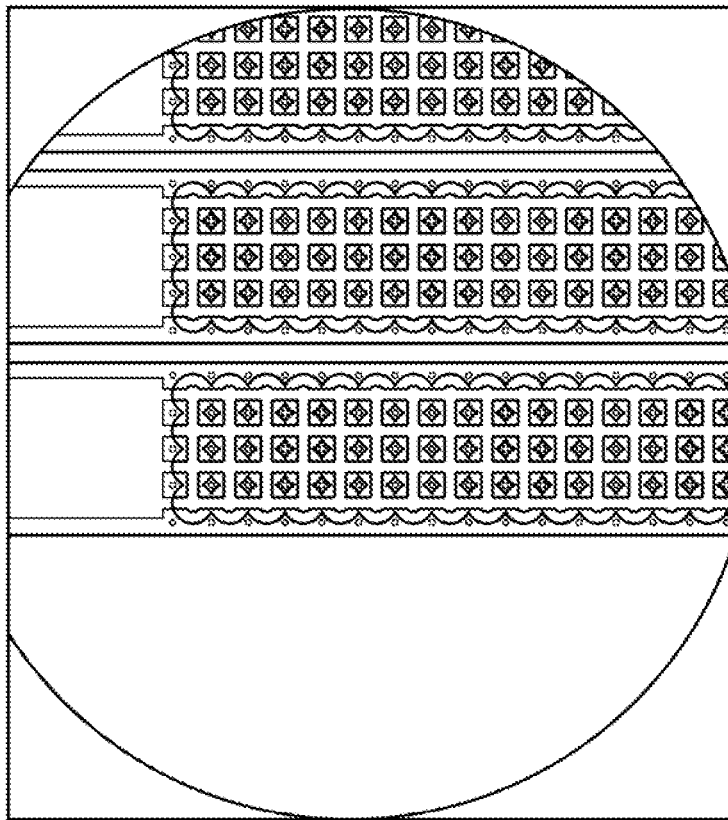

Detailed views of the fabricated arrays are shown in FIG. 40 and FIG. 41 for a 64 and 128 element array, respectively. The diameter of the CMUT cells is 100 µm and 90 µm for the 64 and 128 element arrays, respectively. The thickness of the CMUT membranes is 7.31 µm, which includes the top electrode 16 and the cross-linked areas 15 of the first polymer-based layer 14 and the vacuum-filled cavity 21 has a height of 0.3 µm. Electrical connections for external interface are located at each end on the elements.

Figure 42:
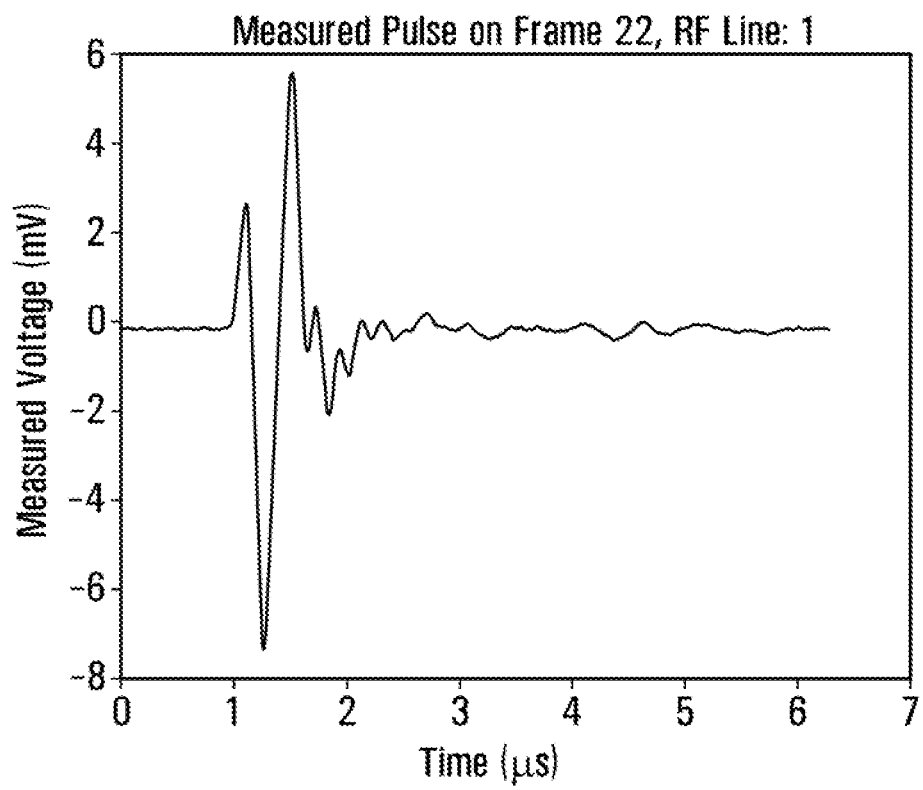
Figure 43:
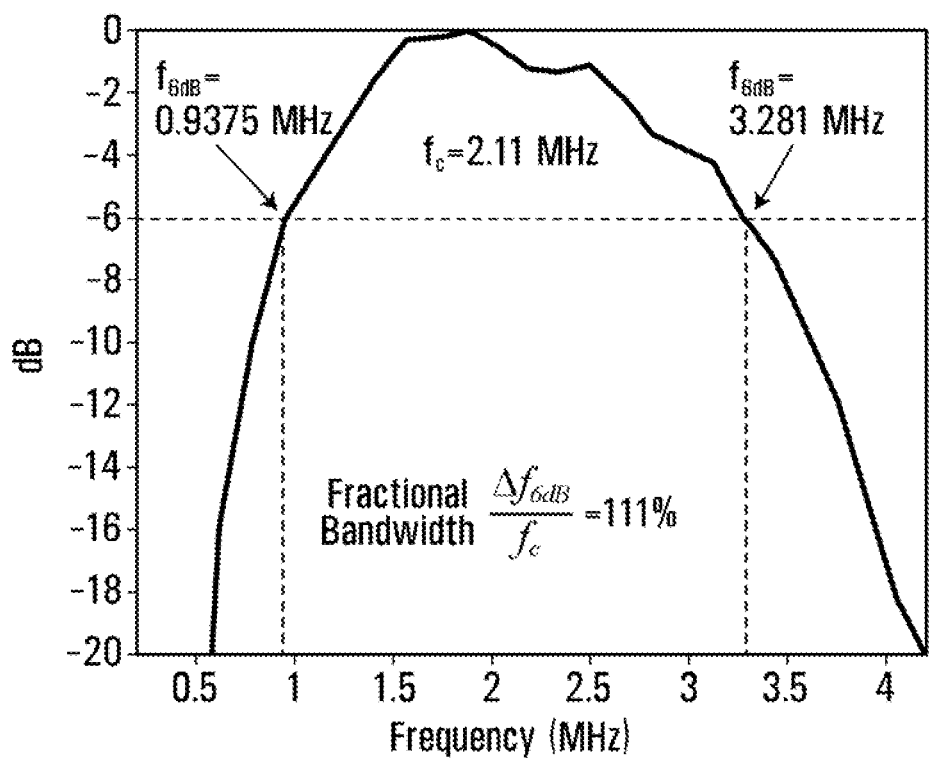

Acoustic measurements were performed in an oil bath using a piezoelectric transducer to validate the operation of the fabricated polymer CMUTs. The measured response is shown in FIG. 42, showing a short pulse characteristic of ultrasound transducers. The frequency spectrum (FFT) of the measured pulse is shown in FIG. 43, having a fractional bandwidth of 111%.

Figure 44:
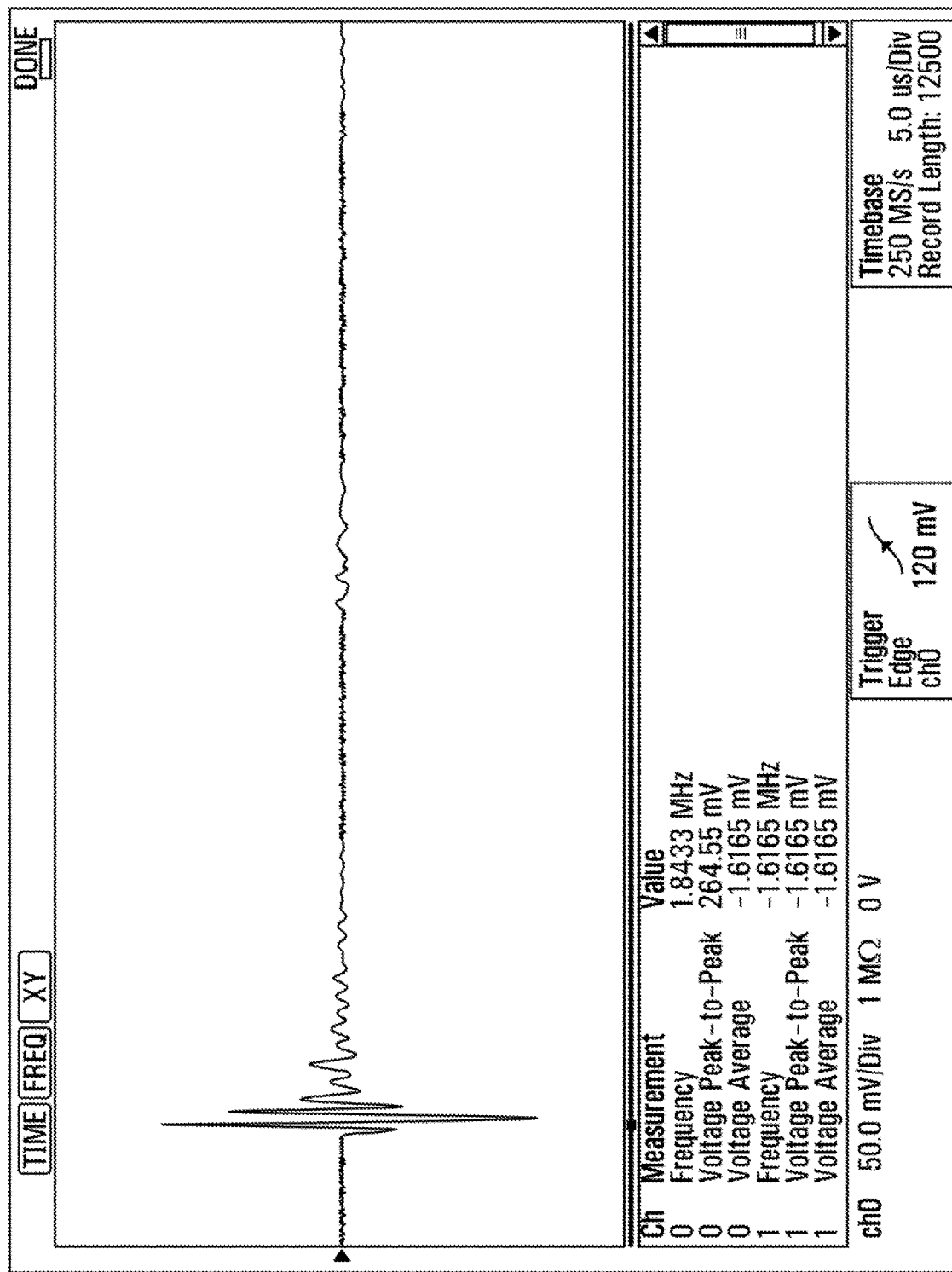

Preliminary results show that it is possible to measure ultrasound pulses using a polymer CMUT element as a passive receiver (i.e., no DC bias voltage applied). FIG. 44 shows the measurement of an ultrasound pulse generated by a piezoelectric crystal located above a polymer CMUT element in a liquid medium operating at an acoustic pressure typical for medical ultrasound imaging. The terminals of the CMUT (top and bottom electrode) were directly connected to an oscilloscope.

The amplitude of the received signal when the CMUTs are operated as a passive device (no DC bias voltage) was 264 mVpp; this represents much more than the expected voltage obtained from typical piezoelectric-based transducers, in which the expected generated voltage across the terminals ranges between a few microvolts and 100 mV. The amplitude of the received signals was increased even further to almost 500 mVpp when a bias voltage of 15V was applied.

This implies that ultrasound signals can be directly processed without the need of low-noise and high-gain amplifiers used in commercial piezoelectric-based ultrasound systems, potentially reducing the physical volume and weight in ultrasound probes and marking a step forward towards a lightweight, low-power conformal ultrasound system.

In at least some embodiments, no acoustic matching layer is required to couple the fabricated CMUTs (regardless of whether fabricated using surface micromachining or wafer bonding) to an aqueous medium. This contrasts with the mandatory acoustic matching layer in conventional piezoelectric-based ultrasound imaging systems.

Additionally, in at least some example embodiments, one or both of the surface micromachining and wafer bonding embodiments may further comprise an annealing operation. When SU8 is used during fabrication, annealing may be done at, for example, 150° C. for five minutes to anneal any cracks that may have formed during development.

The terminology used herein is for the purpose of describing particular embodiments only and is not intended to be limiting. Accordingly, as used herein, the singular forms "a", "an", and "the" are intended to include the plural forms as well, unless the context clearly indicates otherwise. It will be further understood that the terms "comprises" and "comprising", when used in this specification, specify the presence of one or more stated features, integers, steps, operations, elements, and components, but do not preclude the presence or addition of one or more other features, integers, steps, operations, elements, components, and groups. Directional terms such as "top", "bottom", "upwards", "downwards", "vertically", and "laterally" are used in the following description for the purpose of providing relative reference only, and are not intended to suggest any limitations on how any article is to be positioned during use, or to be mounted in an assembly or relative to an environment. Additionally, the term "couple" and variants of it such as "coupled", "couples", and "coupling" as used in this description are intended to include indirect and direct connections unless otherwise indicated. For example, if a first device is coupled to a second device, that coupling may be through a direct connection or through an indirect connection via other devices and connections. Similarly, if the first device is communicatively coupled to the second device, communication may be through a direct connection or through an indirect connection via other devices and connections.

It is contemplated that any part of any aspect or embodiment discussed in this specification can be implemented or combined with any part of any other aspect or embodiment discussed in this specification.

One or more example embodiments have been described by way of illustration only. This description is presented for purposes of illustration and description, but is not intended to be exhaustive or limited to the form disclosed. It will be apparent to persons skilled in the art that a number of variations and modifications can be made without departing from the scope of the claims.

The invention claimed is:

1. A layered structure, comprising:
   (a) a substrate assembly that functions as a bottom electrode;
   (b) a first polymer-based layer suspended above a closed cavity, wherein the closed cavity is between the first polymer-based layer and the substrate assembly;
   (c) a second polymer-based layer placed on the first polymer-based layer, wherein a portion of the second polymer-based layer that is on the first polymer-based layer is thicker than the first polymer-based layer; and
   (d) a top electrode between the first and second polymer-based layers.

2. The structure of claim 1, wherein the top electrode is embedded within the first and second polymer-based layers.

3. The structure of claim 1, wherein the portion of the second polymer-based layer that is on the first polymer-based layer is at least five times thicker than the first polymer-based layer.

4. The structure of claim 1, wherein the cavity has a height selected such that an operating voltage of the structure is no more than 50 Volts.

5. The structure of claim 1, wherein the cavity has a height of no more than 0.3 µm.

6. The structure of claim 1, wherein the cavity is watertight.

7. The structure of claim 1, wherein the substrate assembly comprises a conductive substrate.

8. The structure of claim 1, wherein the substrate assembly comprises a non-conductive substrate and a conductive bottom electrode on the substrate.

9. The structure of claim 1, wherein the substrate assembly comprises an optically-transparent material.

10. The structure of claim 9, wherein the substrate assembly further comprises an optically-transparent conductive bottom electrode on the substrate.

11. The structure of claim 1, wherein the sacrificial layer is non-reactive when exposed to the second polymer-based layer and to a photoresist developer used during the patterning of the second polymer-based layer, and wherein the second polymer-based layer is non-reactive when exposed to an etchant used to etch away the sacrificial layer.

12. The structure of claim 11, wherein the sacrificial layer is also non-reactive when exposed to the first polymer-based layer, and wherein the first polymer-based layer is non-reactive when exposed to the etchant used to etch away the sacrificial layer.

13. The structure of claim 1, wherein the first and second polymer-based layers comprise SU8 photoresist.

14. The structure of claim 1, wherein the sacrificial layer comprises an OmniCoat™ composition.

15. The structure of claim 1, wherein the structure comprises a capacitive micromachined ultrasound transducer and the closed cavity is sealed.

16. The structure of claim 1, wherein the portion of the second polymer-based layer that is on the first polymer-based layer is cross-linked.

* * * * *